(12) United States Patent
Kaveh et al.

(10) Patent No.: US 12,226,126 B2
(45) Date of Patent: Feb. 18, 2025

(54) CANTILEVER PROTRACTION DEVICE

(71) Applicant: Facegenics Inc., Bell Canyon, CA (US)

(72) Inventors: Cameron Kaveh, Bell Canyon, CA (US); Thomas D. Yuschak, Lewis Center, OH (US); Kevin Kaveh, Irvine, CA (US)

(73) Assignee: Facegenics, Inc., Bell Canyon, CA (US)

( * ) Notice: Subject to any disclaimer, the term of this patent is extended or adjusted under 35 U.S.C. 154(b) by 754 days.

(21) Appl. No.: 17/259,432

(22) PCT Filed: Jul. 12, 2019

(86) PCT No.: PCT/US2019/041667
§ 371 (c)(1),
(2) Date: Jan. 11, 2021

(87) PCT Pub. No.: WO2020/014648
PCT Pub. Date: Jan. 16, 2020

(65) Prior Publication Data
US 2021/0275226 A1    Sep. 9, 2021

Related U.S. Application Data

(60) Provisional application No. 62/862,630, filed on Jun. 12, 2019, provisional application No. 62/697,743, filed on Jul. 13, 2018.

(51) Int. Cl.
*A61B 17/66*    (2006.01)
*A61B 17/16*    (2006.01)
(Continued)

(52) U.S. Cl.
CPC ............. *A61B 17/663* (2013.01); *A61C 7/06* (2013.01); *A61C 7/10* (2013.01); *A61B 17/1673* (2013.01);
(Continued)

(58) Field of Classification Search
CPC ....... A61B 17/663; A61B 17/60; A61B 17/66; A61B 17/6416; A61B 17/645;
(Continued)

(56) References Cited

U.S. PATENT DOCUMENTS 415,829 A    11/1889 Angle
664,412 A    12/1900 Knapp
(Continued)

FOREIGN PATENT DOCUMENTS

DE    601 20 845    1/2007
EP    1175874    1/2002
(Continued)

OTHER PUBLICATIONS

U.S. Appl. No. 18/520,328 filed Nov. 27, 2023.
(Continued)

*Primary Examiner* — Marcela I. Shirsat
(74) *Attorney, Agent, or Firm* — EVAN LAW GROUP LLC

(57) ABSTRACT

The present invention provides body anchored protraction devices. The protraction devices direct the negative forces of protraction over a large surface area on the chest and abdomen of a patient. The protraction devices employ a cantilever support rod and ultra-low friction joints to enable low compression on the head without restricting free movement.

20 Claims, 26 Drawing Sheets

(51) Int. Cl.
*A61B 17/17* (2006.01)
*A61B 17/64* (2006.01)
*A61B 17/80* (2006.01)
*A61C 7/06* (2006.01)
*A61C 7/10* (2006.01)
*A61C 7/12* (2006.01)
*A61F 2/30* (2006.01)
*A61F 5/058* (2006.01)
*A61F 5/56* (2006.01)

(52) U.S. Cl.
CPC ......... *A61B 17/176* (2013.01); *A61B 17/6416* (2013.01); *A61B 17/645* (2013.01); *A61B 17/6458* (2013.01); *A61B 17/6466* (2013.01); *A61B 17/6491* (2013.01); *A61B 17/66* (2013.01); *A61B 17/666* (2013.01); *A61B 17/8071* (2013.01); *A61C 7/12* (2013.01); *A61F 2/3099* (2013.01); *A61F 5/05891* (2013.01); *A61F 5/56* (2013.01)

(58) Field of Classification Search
CPC ............ A61B 17/6458; A61B 17/6466; A61B 17/6475; A61B 17/6491; A61B 17/1673; A61B 17/176; A61B 17/666; A61B 17/8071; A61F 5/56; A61F 5/566; A61F 5/05891; A61F 2/3099; A61F 2002/30991; A61F 2002/30993; A61C 7/06; A61C 7/10; A61C 7/065; A61C 7/12
USPC ....... 606/105, 904, 204.15; 433/5, 7, 37–39, 433/43, 49, 54, 57, 58, 60, 61, 66, 67
See application file for complete search history.

(56) References Cited

U.S. PATENT DOCUMENTS

| | | |
|---|---|---|
| 3,303,566 A | 2/1967 | Winkler |
| 3,391,693 A * | 7/1968 | Georgiade ......... A61B 17/6433 602/17 |
| 3,866,322 A | 2/1975 | Broussard et al. |
| 3,977,082 A | 8/1976 | Siatkowski |
| 4,695,250 A | 9/1987 | Mariol |
| 4,815,972 A | 3/1989 | Howe |
| 4,848,368 A | 7/1989 | Kronner |
| 5,564,920 A | 10/1996 | Klapper et al. |
| 5,695,332 A | 12/1997 | Samuels |
| 5,885,290 A | 3/1999 | Guerrero et al. |
| 5,890,891 A * | 4/1999 | Doyle ...................... A61C 7/06 433/5 |
| 5,902,304 A | 5/1999 | Walker et al. |
| 5,904,479 A | 5/1999 | Staples |
| 6,213,765 B1 * | 4/2001 | Standerwick ............ A61C 7/06 433/5 |
| 6,328,745 B1 | 12/2001 | Ascherman |
| 8,529,579 B2 | 9/2013 | Bulloch et al. |
| 8,640,710 B2 | 2/2014 | Matthews |
| 8,662,889 B2 | 3/2014 | Baker |
| 9,333,053 B2 | 5/2016 | Alyami |
| 9,351,810 B2 | 5/2016 | Moon |
| 10,166,089 B2 | 1/2019 | Kahn et al. |
| 10,357,341 B2 | 7/2019 | Alruhaimi |
| 10,433,887 B2 | 10/2019 | Noon et al. |
| 10,575,926 B2 | 3/2020 | Kaveh et al. |
| 10,918,463 B1 | 2/2021 | Alruhimi |
| 2002/0156485 A1 | 10/2002 | Sellers et al. |
| 2003/0050641 A1 | 3/2003 | Mommaerts |
| 2003/0097137 A1 | 5/2003 | Schendel |
| 2003/0138755 A1 * | 7/2003 | Tremont .............. A61C 19/045 433/68 |
| 2005/0021045 A1 | 1/2005 | Schendel |
| 2005/0256526 A1 | 11/2005 | Johnston |
| 2006/0200146 A1 | 9/2006 | Doubler et al. |
| 2007/0287900 A1 | 12/2007 | Breen et al. |
| 2008/0173313 A1 | 7/2008 | Brady |
| 2009/0130620 A1 | 5/2009 | Yazdi et al. |
| 2011/0143300 A1 | 6/2011 | Villaalba |
| 2011/0230885 A1 | 9/2011 | Weiner et al. |
| 2011/0277774 A1 | 11/2011 | Connell |
| 2012/0247490 A1 | 10/2012 | Matthews |
| 2012/0277749 A1 | 11/2012 | Mootien et al. |
| 2013/0252195 A1 | 9/2013 | Popat |
| 2014/0186788 A1 | 7/2014 | Sheibani Nia et al. |
| 2015/0056566 A1 | 2/2015 | Moon |
| 2015/0230831 A1 | 8/2015 | Altarac et al. |
| 2015/0238228 A1 | 8/2015 | Langenfeld |
| 2016/0270883 A1 | 9/2016 | Yousefian |
| 2016/0270884 A1 | 9/2016 | Yousefian |
| 2017/0281315 A1 | 10/2017 | Sotiropoulos |
| 2018/0008376 A1 | 1/2018 | Scommegna |
| 2018/0028282 A1 * | 2/2018 | Kahn .................. A61B 5/0008 |
| 2018/0132978 A1 | 5/2018 | Alruhaimi |
| 2018/0311014 A1 | 11/2018 | Yousefian |
| 2018/0368945 A1 | 12/2018 | Moon |
| 2019/0159873 A1 | 5/2019 | Kaveh et al. |
| 2020/0297388 A1 | 9/2020 | Kaveh |
| 2020/0383710 A1 | 12/2020 | Kaveh |
| 2020/0405449 A1 | 12/2020 | Kaveh |
| 2021/0275226 A1 | 9/2021 | Kaveh et al. |

FOREIGN PATENT DOCUMENTS

| | | |
|---|---|---|
| JP | 2005-204987 | 8/2005 |
| JP | 2017-104417 | 6/2017 |
| KR | 20090068775 | 7/2009 |
| KR | 20110011225 | 2/2011 |
| KR | 10-2011-0126318 | 11/2011 |
| KR | 20160133921 | 11/2016 |
| KR | 10-2017-0066389 | 12/2018 |
| KR | 10-2018-0130375 | 12/2018 |
| WO | 2005/009260 | 2/2005 |
| WO | 2008/011698 | 1/2008 |
| WO | 2016/185018 | 11/2016 |
| WO | 2019/018249 | 1/2019 |
| WO | 2019/104255 | 5/2019 |
| WO | 2019/178008 | 9/2019 |
| WO | 2020/014648 | 1/2020 |

OTHER PUBLICATIONS

Jan. 23, 2019, U.S. Appl. No. 16/115,564.
Mar. 11, 2019, U.S. Appl. No. 16/115,564.
Jul. 17, 2019, U.S. Appl. No. 16/115,564.
Sep. 9, 2019, U.S. Appl. No. 16/115,564.
Jul. 1, 2020, 18822553.6.
Mar. 15, 2021, U.S. Appl. No. 16/630,818.
Nov. 4, 2021, U.S. Appl. No. 16/630,818.
Feb. 28, 2022, U.S. Appl. No. 16/765,805.
Feb. 16, 2022, 18822553.6.
May 24, 2022, U.S. Appl. No. 16/978.746.
May 31, 2021, 201880087707.7.
Aug. 12, 2022, U.S. Appl. No. 16/765,805.
Jan. 17, 2023, U.S. Appl. No. 16/675,805.
Mar. 15, 2023, 18822553.6.
Jan. 10, 2023, 2020-546298.
Dec. 27, 2021, 201980059222.1.
Aug. 16, 20023, U.S. Appl. No. 16/675,805.
Sep. 7, 2023, U.S. Appl. No. 17/259,432.
Nov. 16, 2023, 2018361846.
Jul. 3, 2024 U.S. Appl. No. 17/259,432.
Jul. 17, 2024, U.S. Appl. No. 17/259,432.
Aug. 16, 2024, 18822553.6.
International Search Report and Written Opinion dated Oct. 22, 2018 for PCT application No. PCT/US2018/042200.
International Search Report and Written Opinion dated May 6, 2019 for PCT application No. PCT/US2018/062403.
Moon, W., "Class III treatment by combining facemask (FM) and maxillary skeletal expander (MSE)", Seminars in Orthodontics, vol. 24, issue 1, pp. 95-107, (2018).

(56) References Cited

OTHER PUBLICATIONS

International Search Report and Written Opinion dated Jul. 30, 2019 for PCT application No. PCT/US2019/21707.
International Search Report and Written Opinion dated Nov. 29, 2019 for PCT application No. PCT/US2019/041667.
Extended European Search Report dated Mar. 21, 2022 for EP application No. EP19833137.3.

* cited by examiner

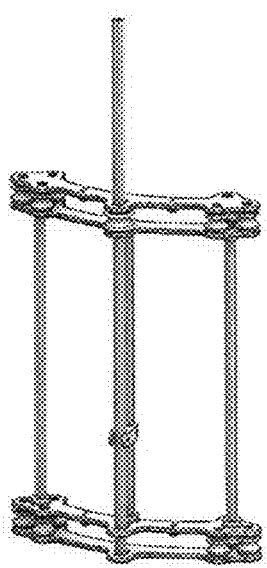 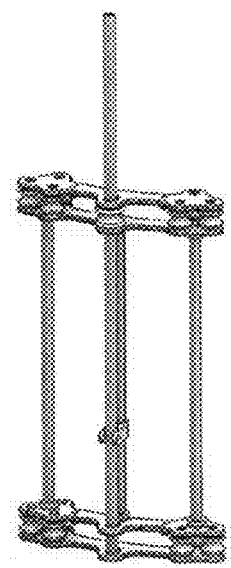 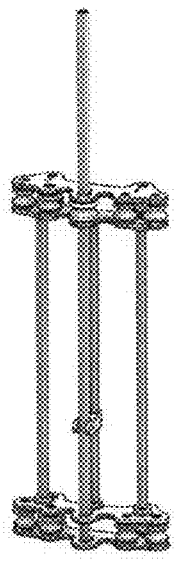
FIG. 14A  FIG. 14B  FIG. 14C
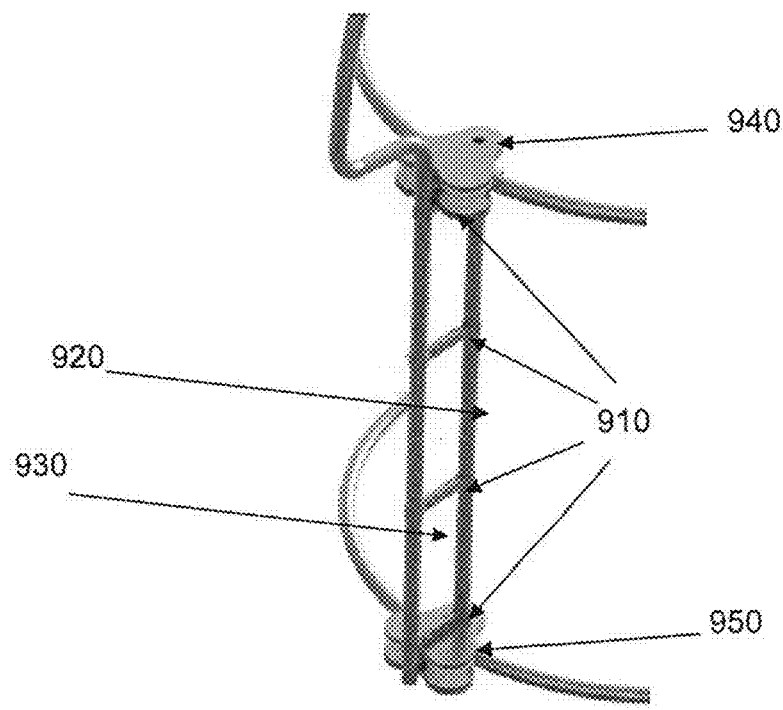
FIG. 15

CANTILEVER PROTRACTION DEVICE

BACKGROUND

A large percentage of people are maxillary deficient relative to their genetic potential for maxillary development. In order to achieve this full maxillary development potential, protractionary forces must be applied to the bone. According to Newton's third law of motion, for every action there is an equal and opposite reaction. Therefore, in order to apply this protractionary force on the maxilla, a device must be capable of handling the opposite reaction.

In traditional orthodontics, convenience has taken priority, and many suboptimal physiologic negative anchorage points have been attempted, including the forehead, cheekbones, chin, and neck. However, applying a negative force to sensitive regions of the body for the long periods of time required for protraction is far from ideal and even harmful in many cases. For example, negative force application on the mandible/chin (such as in U.S. Pat. No. 8,640,710) is associated with mandibular recession and temporomandibular joint stress generation. Devices using a neck brace immobilize the neck and create large amounts of heat and discomfort in the sensitive neck region. Negative force on the frontal bone or cheekbones can create deformation and recession of the bone structure over time. For example, the maxillary protraction device described in U.S. Patent Publication No. 2018/0028282 places significant loads upon the head and provides only limited head movement due to a body anchor having only a single point of articulation anchored to an immobile location on a patient's abdomen.

There is a need in the art for improved protraction devices. The present invention addresses this need.

SUMMARY

In one aspect, the present invention relates to a cantilever protraction device comprising: a frame; a headpiece slidably connected to a headpiece rail having a curvature; and a cantilever support slidably connected to the frame, the cantilever support having an upper end attached to the headpiece rail.

In one embodiment, the frame comprises at least one upper lateral rail and at least one lower lateral rail connected by opposing side rails, the lateral rails being in parallel alignment and having equal curvatures. In one embodiment, the frame is constructed from one or more shaft sections. In one embodiment, at least a portion of the shaft sections are adjustably telescoping.

In one embodiment, the device further comprises at least one strap pad tautly suspended between the opposing side rails, the at least one strap pad comprising padding constructed from a gel or a foam. In one embodiment, the frame comprises a harness having shoulder and waist straps. In one embodiment, the harness and the at least one strap pad are configured to secure the device to a subject such that frame does not physically touch the subject or minimally touches the subject.

In one embodiment, the curvature of the lateral rails is a circular arc having an angle between about 160° and 180°. In one embodiment, the headpiece rail curvature is a circular arc having an angle between about 90° and 140°.

In one embodiment, the device further comprises a linkage arm attached to the headpiece, the linkage arm having a curvature equal to the headpiece rail. In one embodiment, the headpiece further comprises one or more attachments slidably connected to the headpiece rail and lockable to the linkage arm, the one or more attachments selected from a hook attachment, a linear gear bar attachment, and combinations thereof.

In one embodiment, the slidable connections comprise a low friction bearing. In one embodiment, the low friction bearing is constructed from a material selected from polytetrafluoroethylene (PTFE), ultra high molecular weight polyethylene (UHMWPE), and combinations thereof.

In one embodiment, the headpiece is slidable along the headpiece rail in a medial plane and configured to support flexion and extension of a subject's head. In one embodiment, the cantilever support is slidable along the frame along a transverse plane and configured to support rotation of a subject's head. In one embodiment, the attachment between the cantilever support and the headpiece rail comprises a rotatable joint permitting rotation in a coronal plane, the rotatable joint configured to support lateral flexion of a subject's head.

In another aspect, the present invention relates to an anchored protraction device, comprising: a rail having a curvature, the rail being attached to an anchor; a head brace slidably connected to the rail; and an elongate linkage arm attached to the head brace.

In one embodiment, the anchor is securable to a gurney, a bed headboard, a floor stand, and combinations thereof. In one embodiment, the device further comprises one or more attachments slidably connected to the rail and lockable to the linkage arm, the one or more attachments selected from a hook attachment, a linear gear bar attachment, and combinations thereof.

In one embodiment, the slidable connections comprise a low friction bearing. In one embodiment, the low friction bearing is constructed from a material selected from polytetrafluoroethylene (PTFE), ultra high molecular weight polyethylene (UHMWPE), and combinations thereof.

In a third aspect, the invention is a protraction device comprising a body frame and a cantilever support. The body frame is adapted to be anchored to the body of a patient. The cantilever support includes a first shaft, coupled to the body frame, and a second shaft, coupled to the first shaft. The second shaft extends in front of the face of the patient.

In a fourth aspect, the invention is a protraction system comprising a therapeutic appliance, a protraction device, and a force applicator. The therapeutic appliance is coupled to a patient. The protraction device includes a body frame and a cantilever support, coupled to the body frame by a roller bearing. The force applicator is removably coupled to the cantilever support and to the therapeutic appliance. The therapeutic appliance is anchored to at least one member selected from the group consisting of the teeth, bone, and soft tissue of the patient.

In a fifth aspect, the invention is a method of providing maxillary protraction to a patient in need thereof comprising coupling a protraction device to a therapeutic appliance. The therapeutic appliance is coupled to the patient.

In a sixth aspect, the invention is a headpiece comprising a first strap, a harness, and a second strap. The first strap is configured to encircle the back and sides of the head of a patient. The harness is removably coupled to the first strap by a plurality of fasteners. The second strap is configured to pass under the jaw of the patient and is coupled to the harness. The second strap comprises a mandible fastener. The harness does not obstruct the facial area of the patient.

In a seventh aspect, the invention is a protraction device comprising an anchor, a cantilever support, a headpiece, and a force applicator. The cantilever support includes a shaft movably coupled to the anchor. The headpiece is adjustably coupled to the shaft. The force applicator is removably coupled to the headpiece and adjustably coupled to the shaft. The anchor is configured to be secured to a supporting object.

In an eighth aspect, the invention is a protraction system comprising a therapeutic appliance and a trans-oral member. The therapeutic appliance is adapted to be coupled to at least one member selected from the group consisting of the teeth, bone, and soft tissue of a patient. The trans-oral member includes a curved member and an extra-oral vertical member. Each end of the curved member is coupled to opposing ends of the therapeutic appliance. The extra-oral vertical member extends vertically from the plane of the curved member.

BRIEF DESCRIPTION OF THE DRAWINGS

The following detailed description of embodiments of the invention will be better understood when read in conjunction with the appended drawings. It should be understood, however, that the invention is not limited to the precise arrangements and instrumentalities of the embodiments shown in the drawings.

FIG. 14A illustrates a cantilever support with multiple bearings having a separation angle of 60°.

FIG. 14B illustrates a cantilever support with multiple bearings having a separation angle of 45°.

FIG. 14C illustrates a cantilever support with multiple bearings having a separation angle of 30°.

FIG. 15 illustrates a cantilever support with support bars.

DETAILED DESCRIPTION

Figure 1:
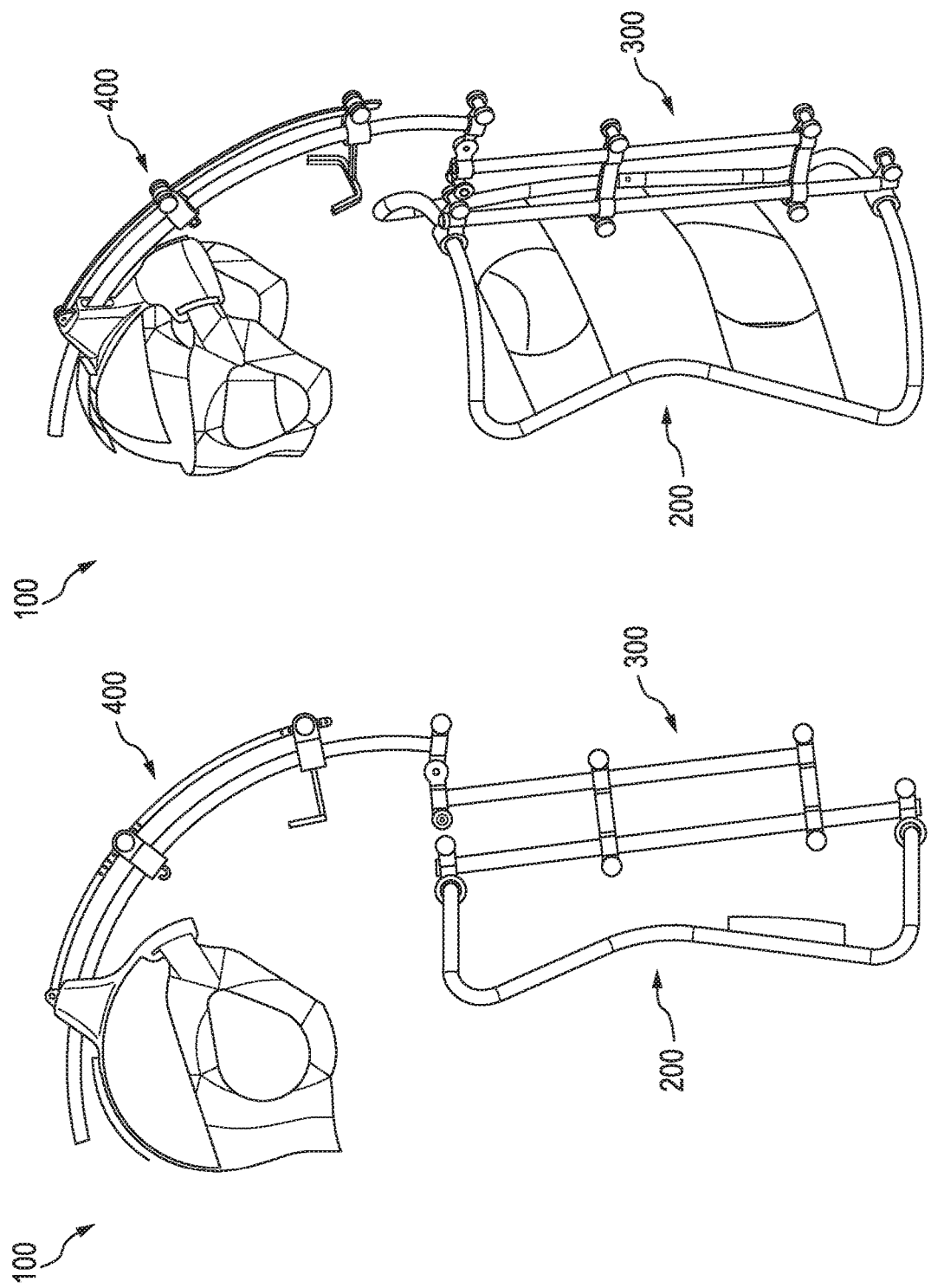
FIG. 1 depicts a side view (left) and a perspective view (right) of an exemplary protraction device.

The present invention provides body anchored protraction devices and off-the-head anchored protraction devices. The protraction devices direct the negative forces of protraction over a large surface area on the chest and abdomen of a patient. The protraction devices are lightweight and employ a cantilever support rod and ultra-low friction joints to enable low compression on the head with low resistance to head movements.

Definitions

It is to be understood that the figures and descriptions of the present invention have been simplified to illustrate elements that are relevant for a clear understanding of the present invention, while eliminating, for the purpose of clarity, many other elements typically found in the art. Those of ordinary skill in the art may recognize that other elements and/or steps are desirable and/or required in implementing the present invention. However, because such elements and steps are well known in the art, and because they do not facilitate a better understanding of the present invention, a discussion of such elements and steps is not provided herein. The disclosure herein is directed to all such variations and modifications to such elements and methods known to those skilled in the art.

Unless defined elsewhere, all technical and scientific terms used herein have the same meaning as commonly understood by one of ordinary skill in the art to which this invention belongs. Although any methods and materials similar or equivalent to those described herein can be used in the practice or testing of the present invention, exemplary methods and materials are described.

As used herein, each of the following terms has the meaning associated with it in this section.

The articles "a" and "an" are used herein to refer to one or to more than one (i.e., to at least one) of the grammatical object of the article. By way of example, "an element" means one element or more than one element.

"About" as used herein when referring to a measurable value such as an amount, a temporal duration, and the like, is meant to encompass variations of ±20%, ±10%, ±5%, ±1%, and ±0.1% from the specified value, as such variations are appropriate.

The term "supporting object" means an object having a rigid surface that is capable of physically supporting an anchored protraction device. Examples of supporting objects include walls, beds, gurneys and stands, such as floor stands.

Throughout this disclosure, various aspects of the invention can be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6, etc., as well as individual numbers within that range, for example, 1, 2, 2.7, 3, 4, 5, 5.3, 6, and any whole and partial increments therebetween. This applies regardless of the breadth of the range.

Protraction Device

The present invention provides protraction devices that are configured to direct the negative forces of maxillary protraction to the chest and abdomen and away from the sensitive regions of the head and neck of a patient. The devices spread the negative force out over a large surface area to reduce fatigue and discomfort. Wearable devices are lightweight, such as in the range of 1 to 2 lbs and below, and permit a patient's head to retain substantial freedom of motion, including rotation and nodding. Referring now to FIG. 1, an exemplary body anchored protraction device 100 is depicted. Device 100 comprises body frame 200, cantilever support 300, and headpiece 400.

Figure 2:
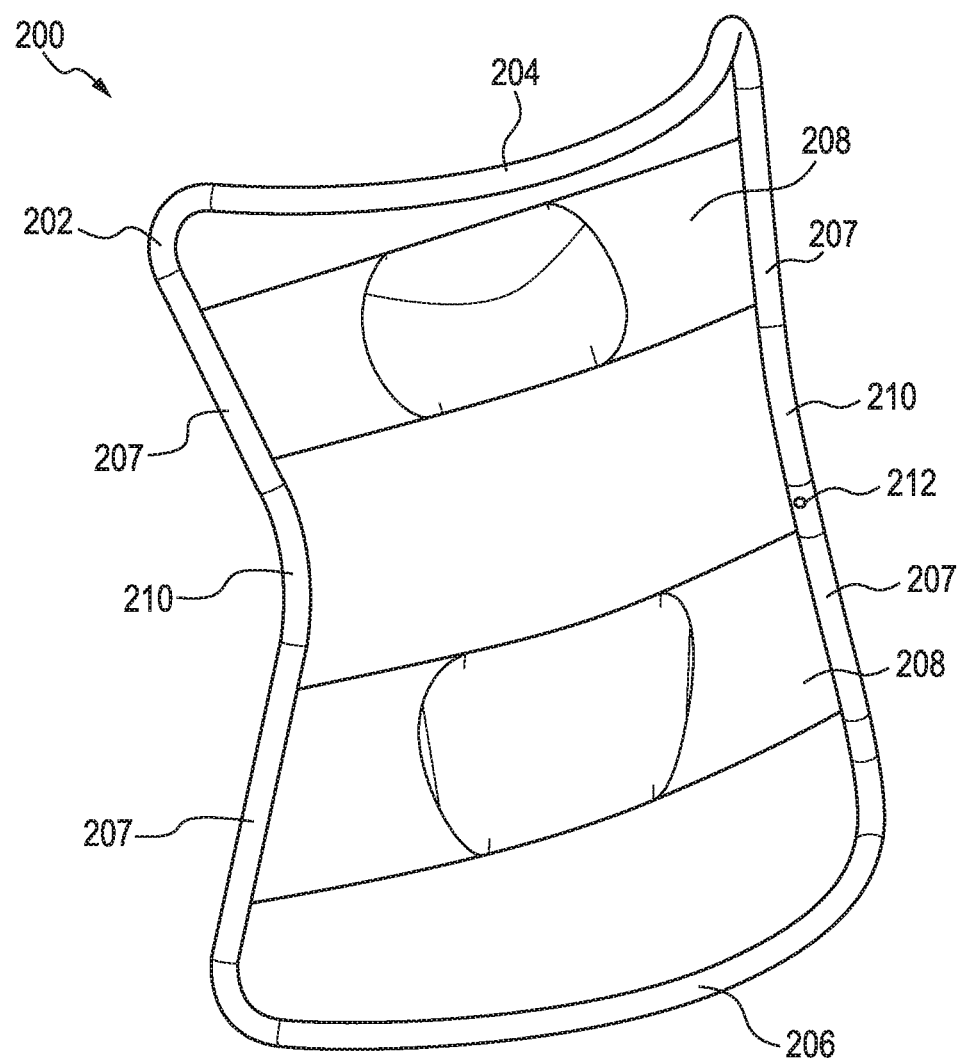
FIG. 2 depicts a perspective view of an exemplary body frame of a protraction device.

Referring now to FIG. 2, body frame 200 is described in detail. Body frame 200 comprises one or more sections of shaft 202 forming a perimeter. Body frame 200 can have any suitable shape, such as a substantially quadrilateral or elliptical shape. Shaft 202 can be hollow or solid and can be constructed from any suitably rigid material, such as aluminum, polycarbonate, or some other lightweight metal, plastic, or composite material. In various embodiments, shaft 202 can have any suitable cross section, including circular, elliptical, square, and rectangular. At a top side and a bottom side, shaft 202 forms upper rail 204 and lower rail 206, respectively, each connected to opposing side rails 207. Upper rail 204 and lower rail 206 are aligned in parallel (see FIG. 1) and have matching curvatures. In some embodiments, the matching curvatures can be described as a circular arc having an angle between about 160° and 180°. In some embodiments, body frame 200 can comprise one or more additional lateral rails aligned in parallel with upper rail 204 and lower rail 206 and having matching curvatures. The one or more additional lateral rails can be connected to side rails 207, or to upper rail 204 or lower rail 206, such as by a short segment of shaft 202. Side rails 207 can have one or more indents 210 configured to conform to a patient's anatomy, such as the pectoral muscles.

Figure 3:
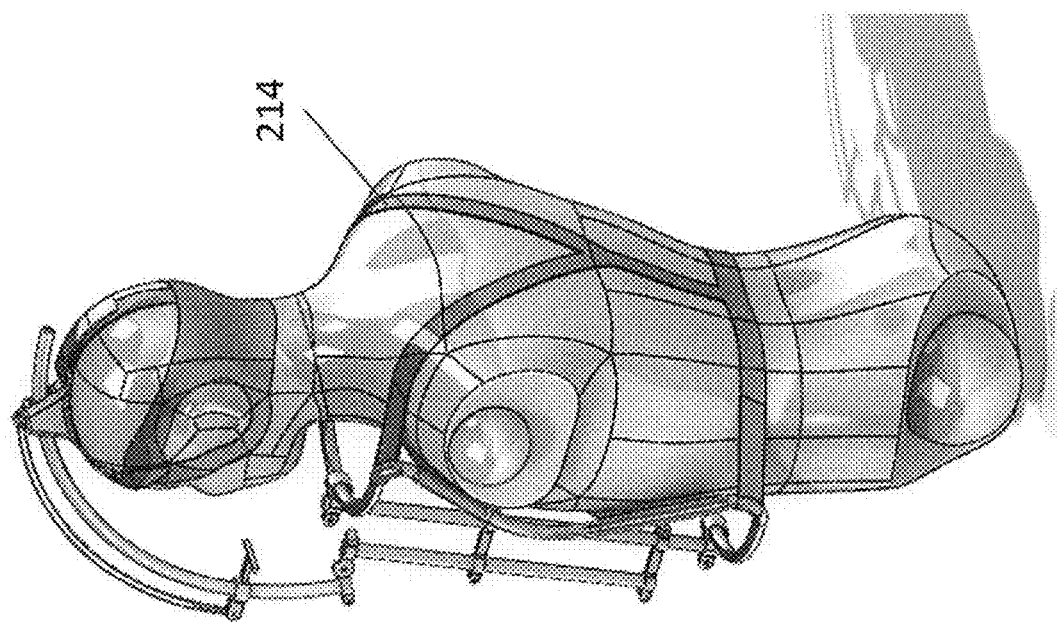
FIG. 3 depicts a front view (left) and a back view (right) of an exemplary protraction device fitted to a patient with a harness.
Figure 3:
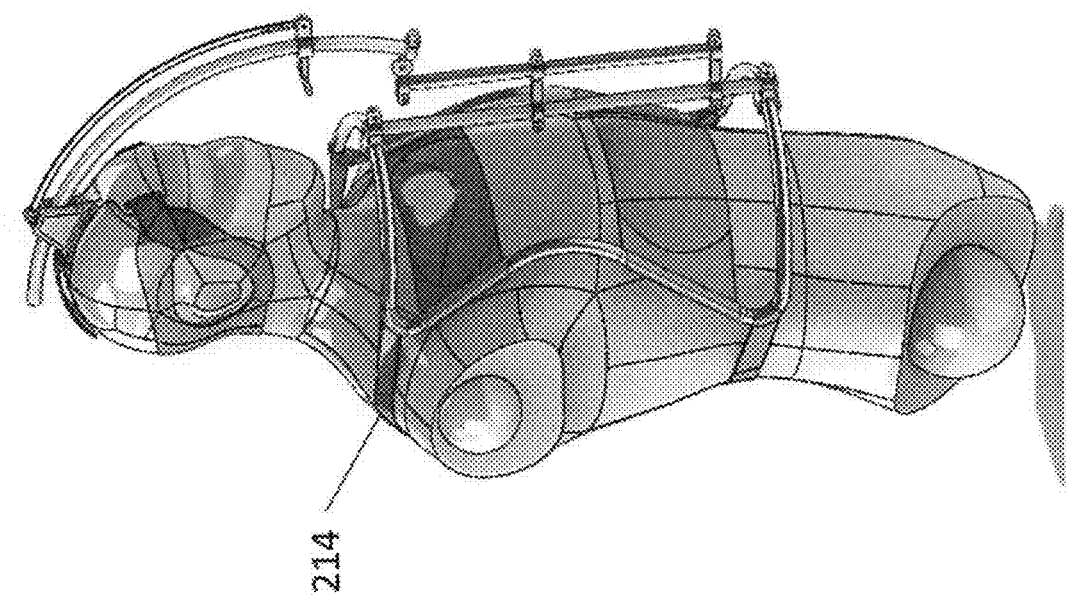

Body frame 200 can be secured to a patient's body using any suitable mechanism. For example, in some embodiments body frame 200 further comprises strap pads 208 suspended between side rails 207. Strap pads 208 can be constructed from a fabric or polymer mesh and can be fitted with a gel or foam cushion for enhanced comfort and fit. In some embodiments, strap pads 208 are suspended in a taut fashion to support the weight of device 100 and to support lateral forces exerted on device 100. In another example, body frame 200 can comprise a plurality of rigid or semi-rigid padded feet configured to engage the shoulder and abdomen of a patient and to support and spread out the lateral forces exerted on device 100. In some embodiments, body frame 200 is size adjustable, wherein sections of shaft 202 are telescoping and lockable by way of one or more locks 212. Body frame 200 further comprises harness 214 having shoulder and waist straps to secure body frame 200 to a patient (FIG. 3). It should be noted that appropriate sizing and fit of body frame 200 secures device 100 to a patient such that frame 200 does not physically contact the patient, or minimally contacts the patient, ensuring that loads are spread out over the patient's body.

Figure 4:
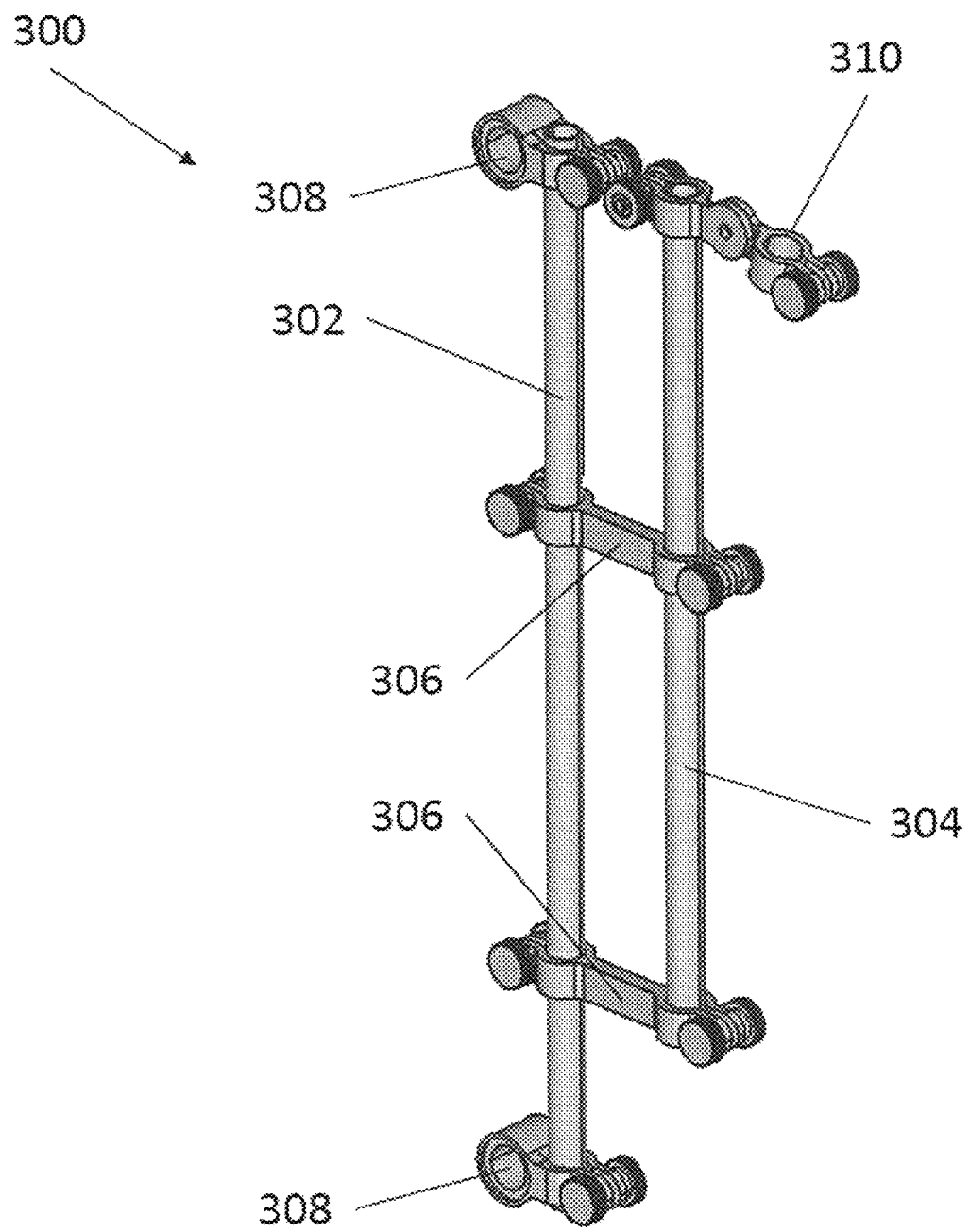
FIG. 4 depicts a perspective view of an exemplary cantilever support of a protraction device.

Referring now to FIG. 4, cantilever support 300 is described in detail. Cantilever support 300 comprises first shaft 302 and second shaft 304 secured to each other by clamps 306. Similarly to shaft 202, first shaft 302 and second shaft 304 can be constructed from any suitably rigid and lightweight material. First shaft 302 comprises low friction bearing 308 at its upper and lower ends, wherein the upper low friction bearing 308 is slidable along upper rail 204 and the lower low friction bearing 308 is slidable along lower rail 206. In various embodiments, first shaft 302 can comprise additional low friction bearings 308 connectable to and slidable along additional lateral rails on body frame 200, as described elsewhere herein. Each low friction bearing 308 can be constructed from any durable material having a low coefficient of friction, such as polytetrafluoroethylene (PTFE) and ultra high molecular weight polyethylene (UHMWPE). Second shaft 304 comprises headpiece attachment 310 at its upper end. The positioning of the various components (clamps 306, low friction bearing 308, headpiece attachment 310) are adjustable along their respectively attached first shaft 302 or second shaft 304 by any suitable locking mechanism, such as a ring clamp.

Figure 5:
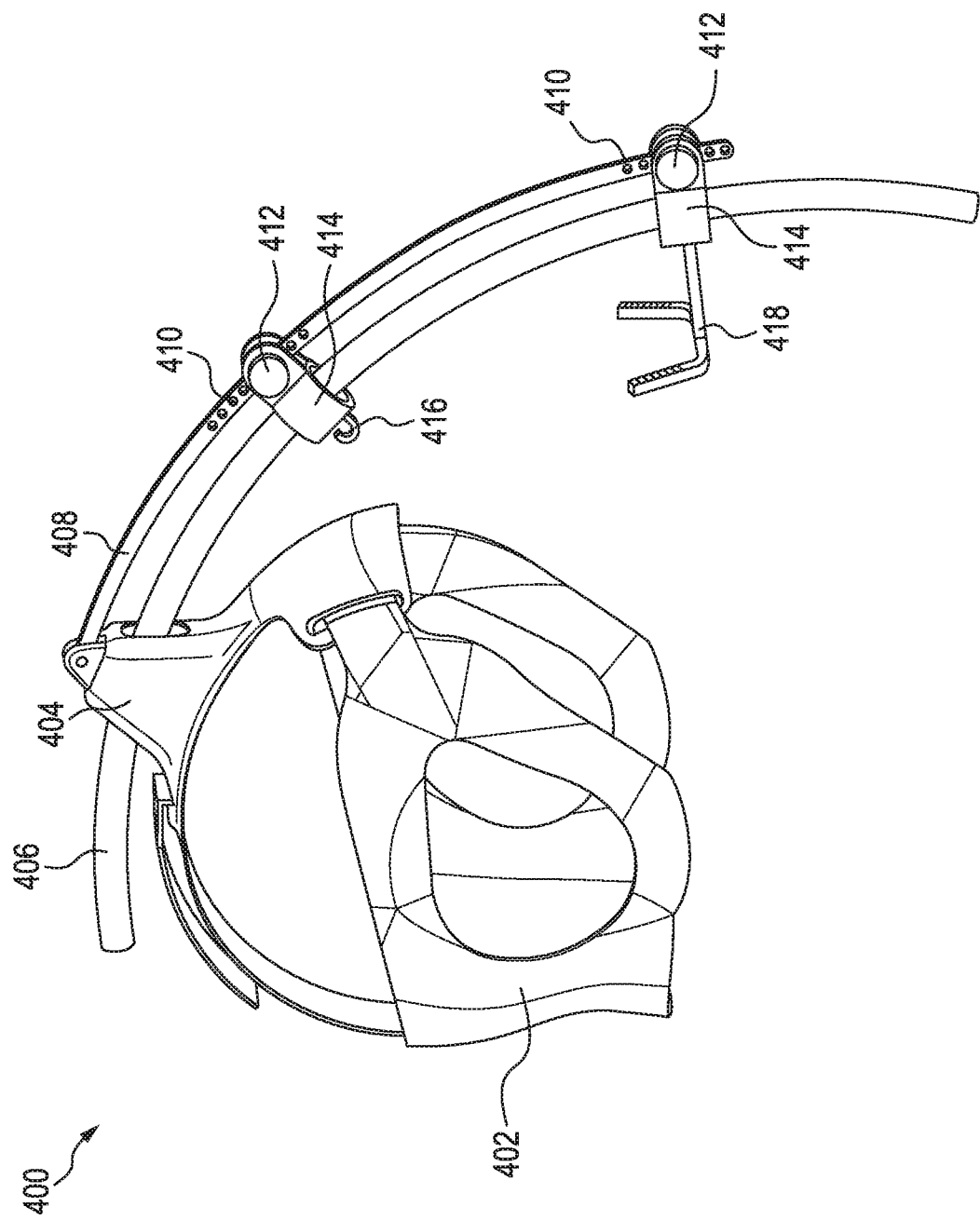
FIG. 5 depicts a perspective view of an exemplary headpiece of a protraction device.
Figure 6:
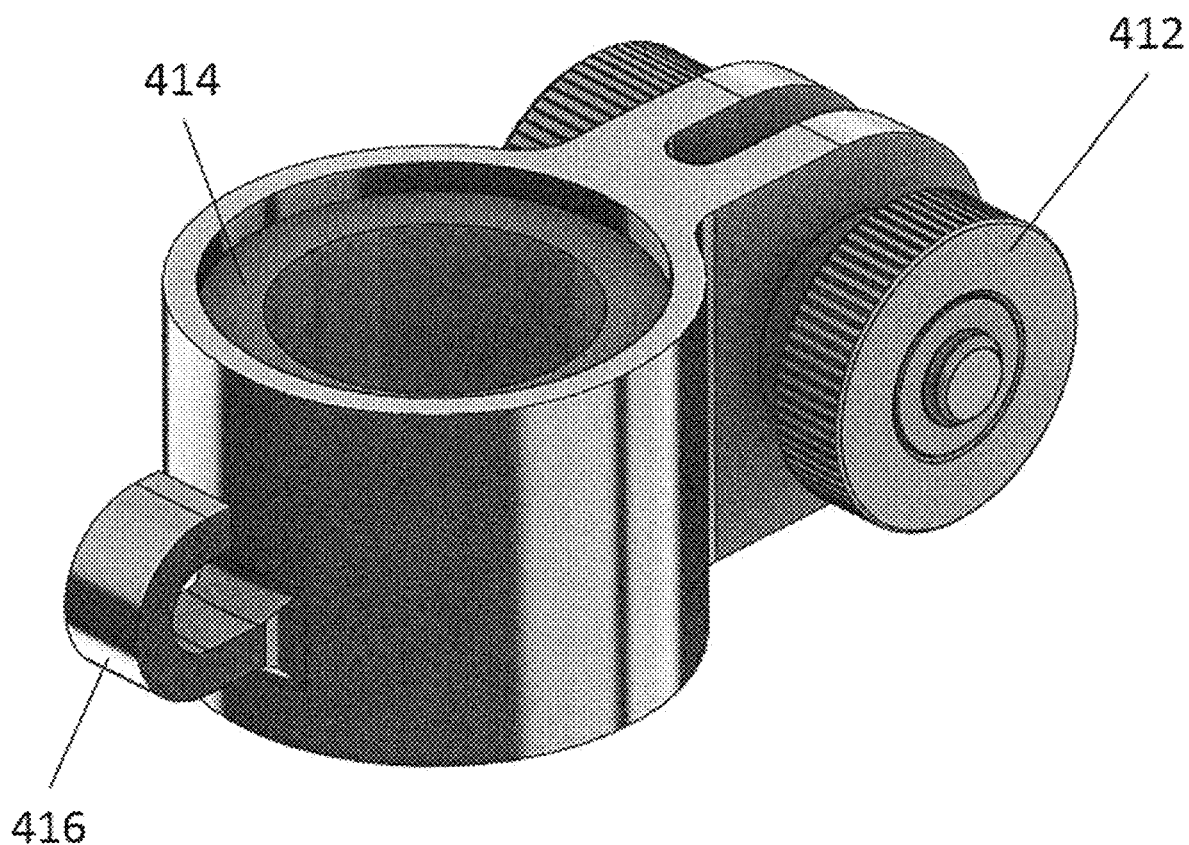
FIG. 6 depicts a perspective view of an exemplary low friction bearing with hook attachment.
Figure 7:
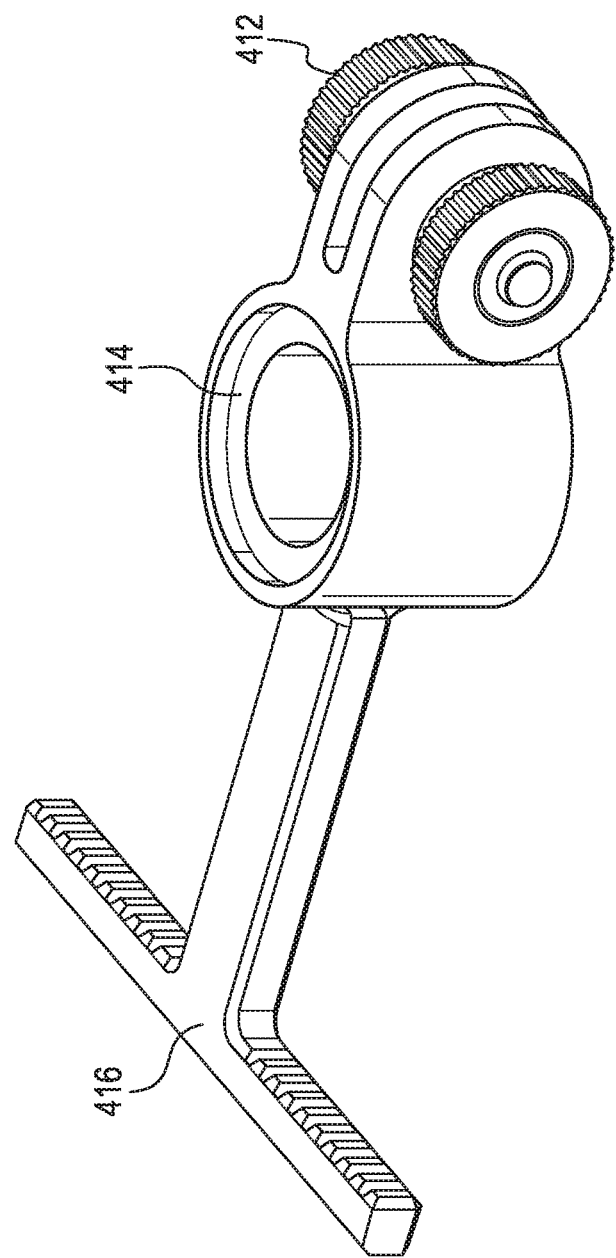
FIG. 7 depicts a perspective view of an exemplary low friction bearing with rack attachment.
Figure 8:
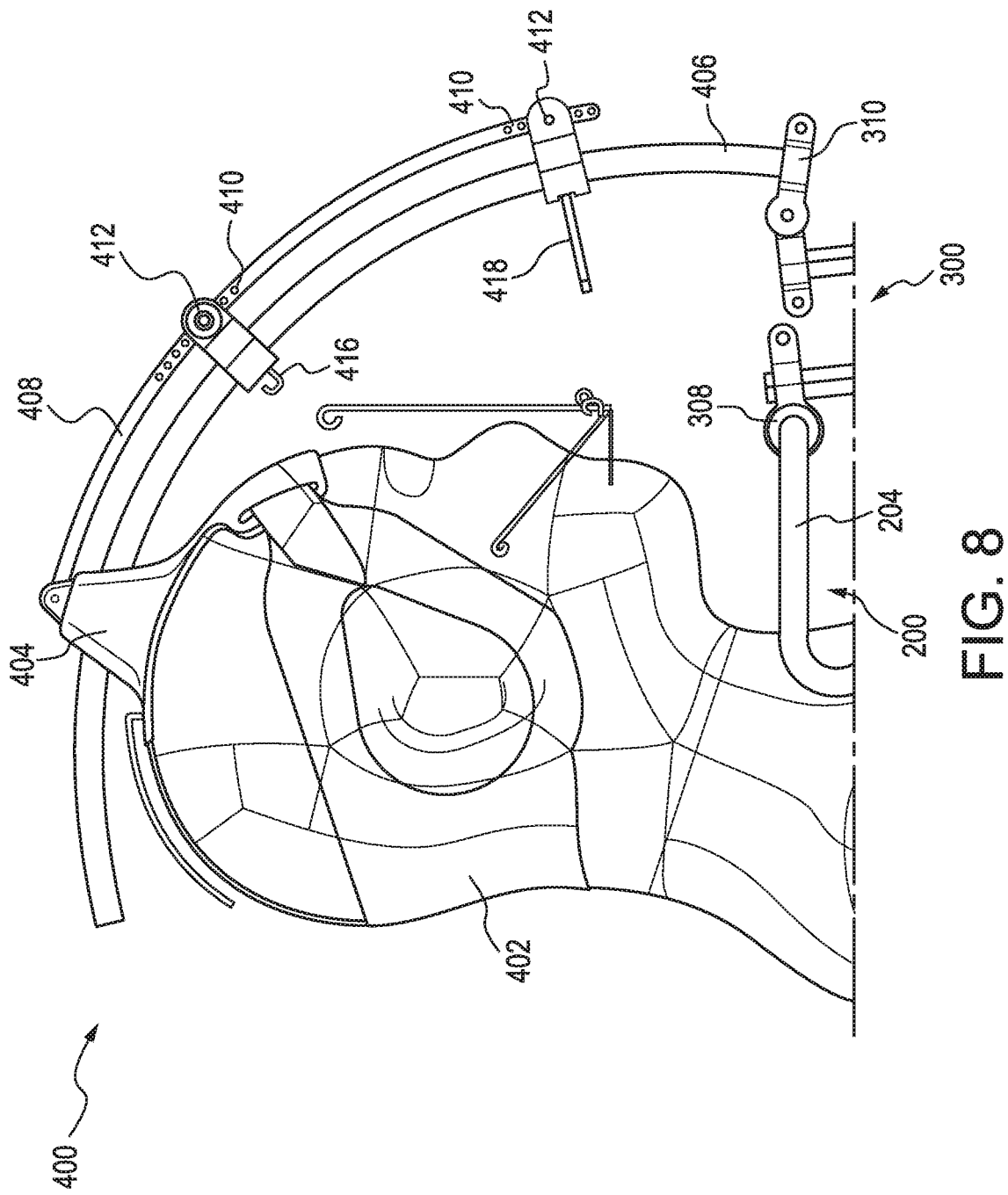
FIG. 8 depicts a side view of an exemplary headpiece attached to the head of a patient.

Referring now to FIG. 5, headpiece 400 is described in detail. Headpiece 400 comprises head strap 402 attached to rail guide 404. Head strap 402 is a flexible piece that is configured to wrap around a patient's head and holds rail guide 404 securely to the top of the patient's head. Rail guide 404 has a lumen sized to fit rail 406 and is connected to linkage bar 408. In some embodiments, rail guide 404 comprises a low friction bearing within its lumen. Rail 406 and linkage bar 408 are aligned in parallel and share the same curvature. In some embodiments, the matching curvature can be described as a circular arc having an angle between about 90° and 140°. Rail 406 has a lower end that is attachable to headpiece attachment 310 of cantilever support 300. Linkage bar 408 comprises a plurality of holes 410 along its curvature, each hole 410 being sized to fit a pin or screw from a lock 412. Each lock 412 comprises a low friction bearing 414 that is slidable along rail 406. In some embodiments, headpiece 400 comprises at least a first lock 412 having a hook attachment 416 and a second lock 412 having a linear gear bar attachment 418. Hook attachment 416 (shown in greater detail in FIG. 6) provides a point of attachment for a string, wire, or elastic band, and can include a simple hook, a closed loop, or a spring-loaded gate (such as a carbiner design). Linear gear bar attachment 418 (shown in greater detail in FIG. 7) comprises one or more toothed bars to provide a variable point of attachment for a string, wire, or elastic band. Hook attachment 416 and linear gear bar attachment 418 are each connectable to a maxillary protraction device. The negative forces exerted on a maxillary protraction device can thereby be tuned by adjusting the position of each lock 412 with each hole 410 along the curvature of linkage bar 408. For example, in one embodiment depicted in FIG. 8, hook attachment 416 can be positioned between about 30° and 90° relative to a transverse plane, and linear gear bar attachment 418 can be positioned between about −35° and 60° relative to a transverse plane.

Combining body frame 200, cantilever support 300, and headpiece 400, protraction device 100 is capable of comfortably applying protractionary forces to a patient without loading sensitive head and neck regions while permitting substantial freedom of movement in the patient's head. Locking each component on cantilever support 300 enables cantilever support 300 to be laterally slidable on body frame 200 as a single rigid unit by virtue of the slidable connection between its upper low friction bearing 308 to upper rail 204 and its lower low friction bearing 308 to lower rail 206. With respect to headpiece 400, head strap 402, rail guide 404, and each of the locks 412 can be locked in place relative to each other by way of linkage bar 408, and the locked assembly is configured to be freely slidable along rail 406. Device 100 thereby enables a patient to perform a shaking gesture along the curvature of upper rail 204 and lower rail 206 in the transverse plane to rotate the head left and right and a nodding gesture along the curvature of rail 406 in the median plane between flexion, extension, and hyper-extension of the neck. In some embodiments, headpiece attachment 310 further comprises a rotatable joint to permit a head tilting gesture in the coronal plane (i.e., lateral flexion). In some embodiments, one or more of clamps 306 can include a tension spring, or rotatable joints at headpiece attachment 310 and rail guide 404 can permit additional anterior and posterior head movement in the median plane (i.e. a pecking motion).

Figure 9:
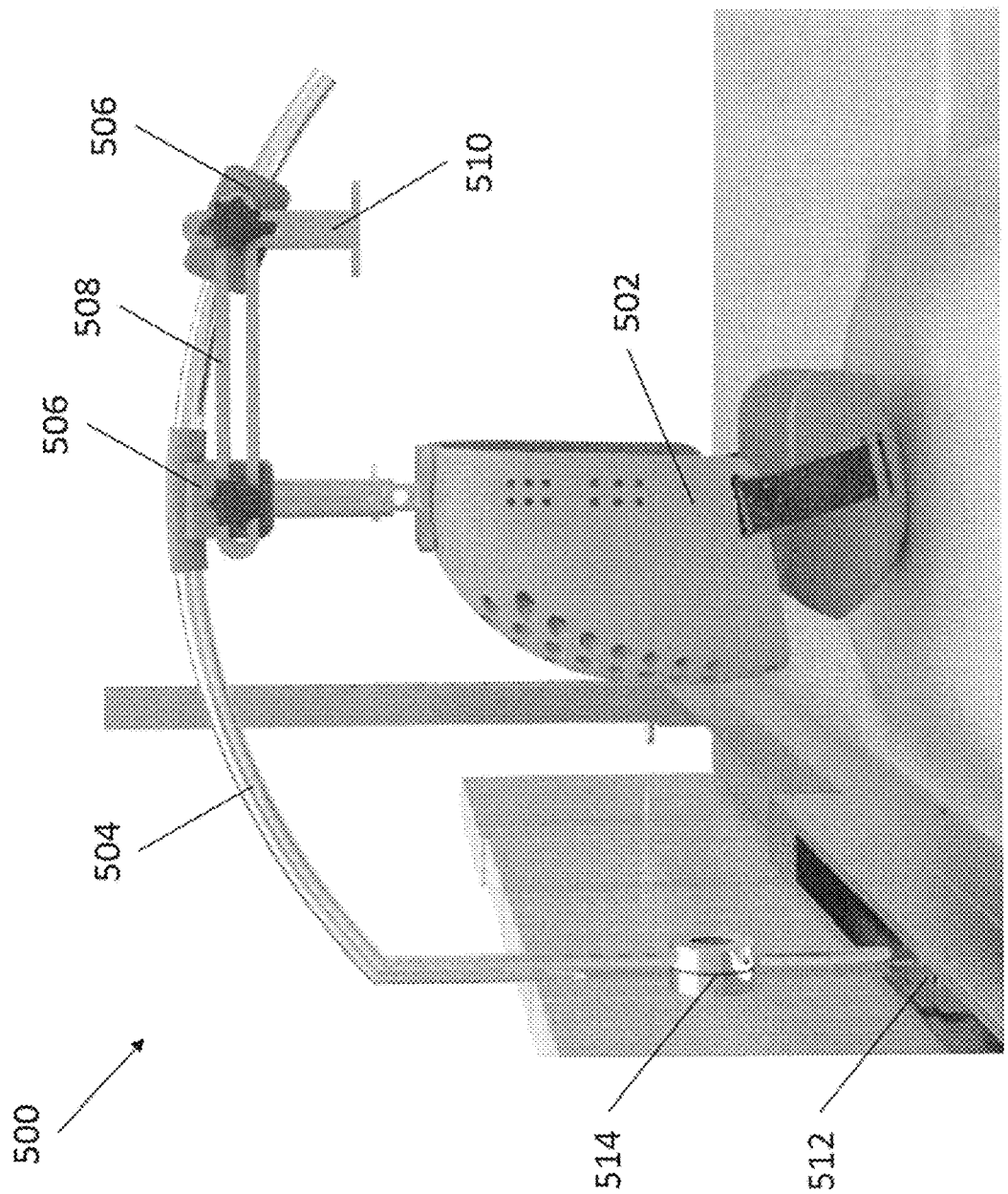
FIG. 9 depicts a side view of another exemplary protraction device.

Referring now to FIG. 9, another protraction device 500 is depicted. Protraction device 500 employs similar components as device 100 that can be anchored to a bed, gurney, or floor stand. Device 500 comprises head brace 502 attached to a curved rail 504 by a first lock 506. Device 500 comprises one or more additional locks 506, wherein each lock 506 is lockable relative to each other to linkage bar 508. Locks 506 can each comprise a maxillary device attachment 510 to support loads for maxillary protraction. Rail 504 can be immobilized by anchor 512 to a headboard, floor stand, wall, or any suitable rigid structure. Rail 504 further comprises rotating hinge 514 to permit a patient to change sleeping positions while maintaining protractionary forces.

Additional research has identified optional modifications to the innovative cantilevered protraction device described above. A number of improvements have been developed that will enhance the functionality and durability of the device and improve the experience for the user.

Figure 11A:
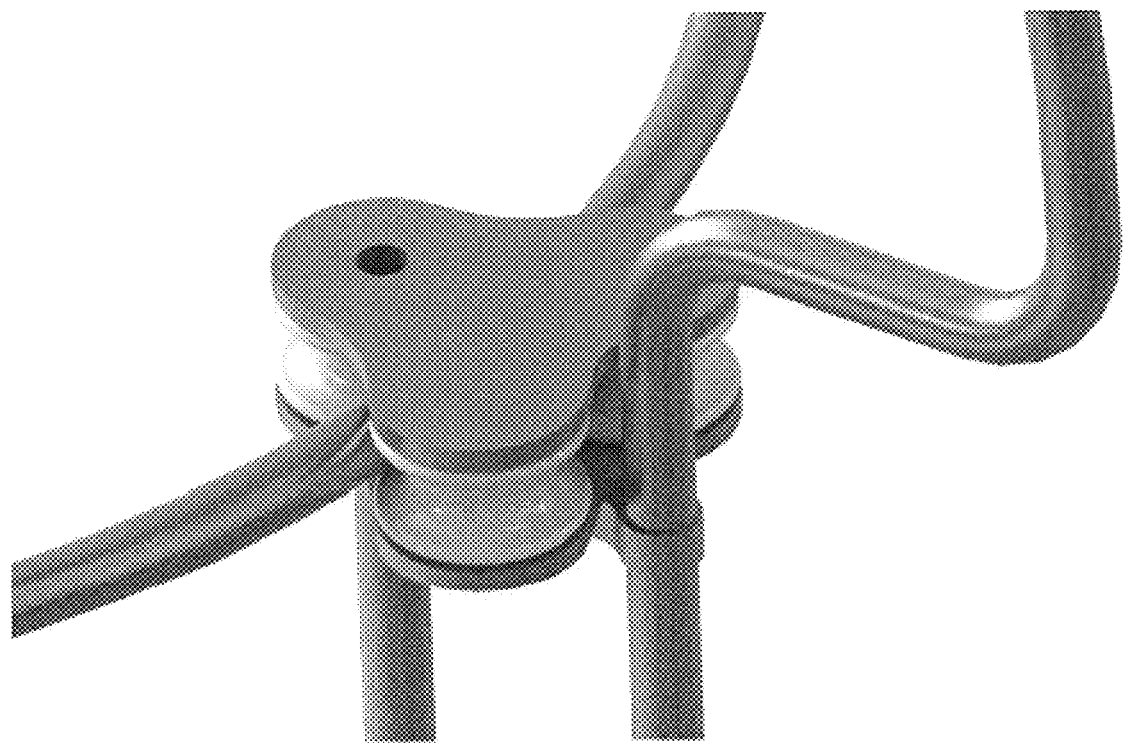
FIG. 11A illustrates a perspective view of a cantilevered protraction device with a roller bearing.
Figure 11B:
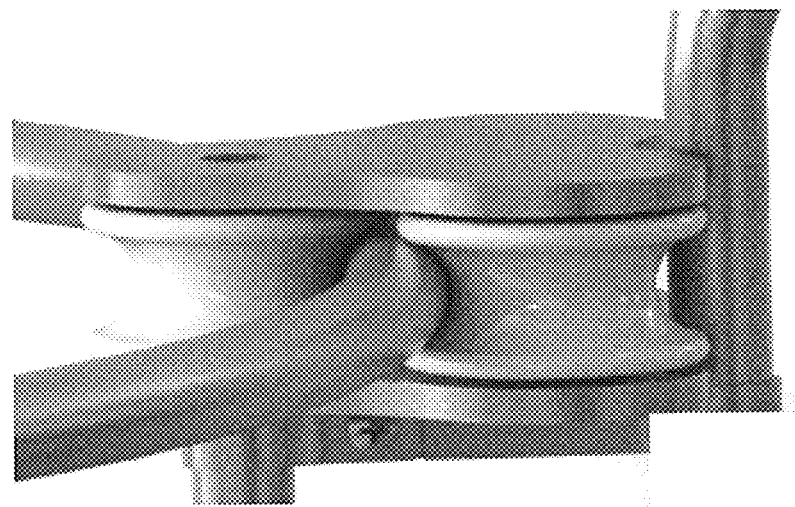
FIG. 11B illustrates a side view of a cantilevered protraction device with a roller bearing.

The lateral movement of the cantilever support along the body frame may be improved by the use of roller bearings. FIG. 11A illustrates a perspective view of a cantilevered protraction device with a roller bearing. FIG. 11B illustrates a side view of a cantilevered protraction device with a roller bearing. Roller bearings have a lower coefficient of friction than sliding bearings (such as the slider bearings shown in FIG. 4 as element 308 and in FIG. 5 as element 414), which allows for more fluid motion when moment loads are applied.

Figure 11C:
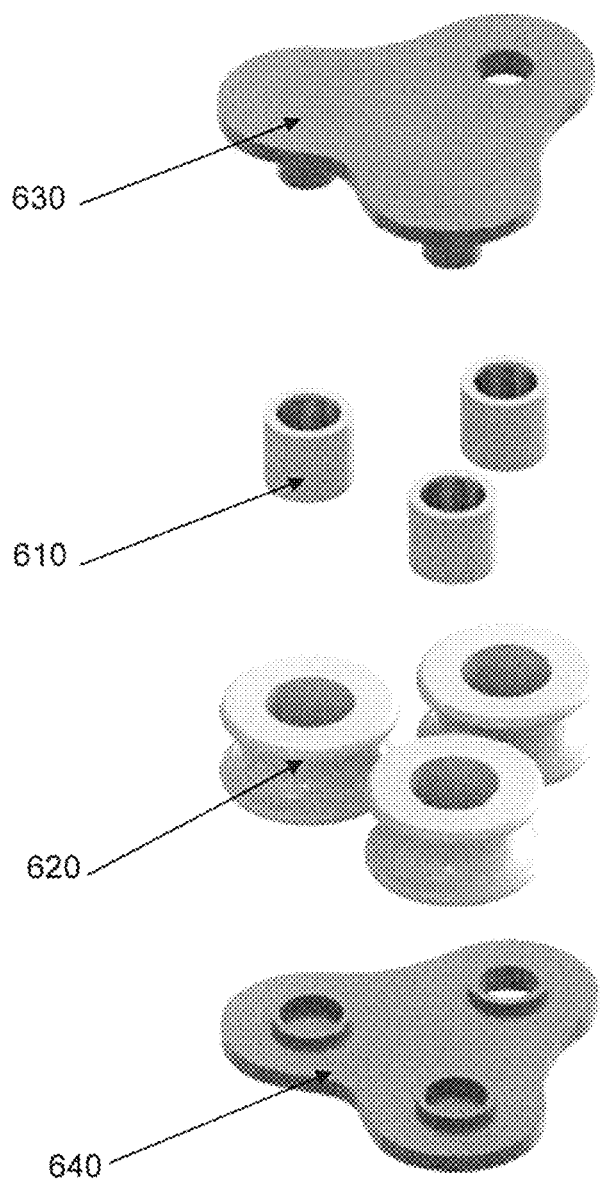
FIG. 11C illustrates an exploded view of a roller bearing.

FIG. 11C illustrates an exploded view of a roller bearing. The roller bearing includes one or more needle bearings 610 surrounded by an equal number of rollers 620 coupled to an upper plate 630 and a lower plate 640. The components of the roller bearing may be coupled together using any suitable types of fasteners, such as screws or bolts. The upper and lower plates may be formed from any rigid, durable material such as metals, plastics or ceramics. Preferably, the upper and lower plates are made of plastic or aluminum. The rollers may be formed from any rigid, durable material such as metals, plastics or ceramics. Preferably, the rollers are made from plastic, aluminum or brass. The roller bearing may optionally include a low-friction substance between the rollers and the upper and lower plates to facilitate the motion of the rollers. The low-friction substance may be any material with a low coefficient of friction. Examples of suitable low-friction substances include polytetrafluoroethylene (PTFE or TEFLON®), ultra high molecular weight polyethylene (UHMWPE), polyimide, polyether ether ketone (PEEK), polyphenylene sulfide (PPS), nylon, polyoxymethylene (POM or acetal), polyesters, acrylonitrile butadiene styrene (ABS), polycarbonate (PC) or polycarbonate/ABS (PC/ABS).

Figure 12:
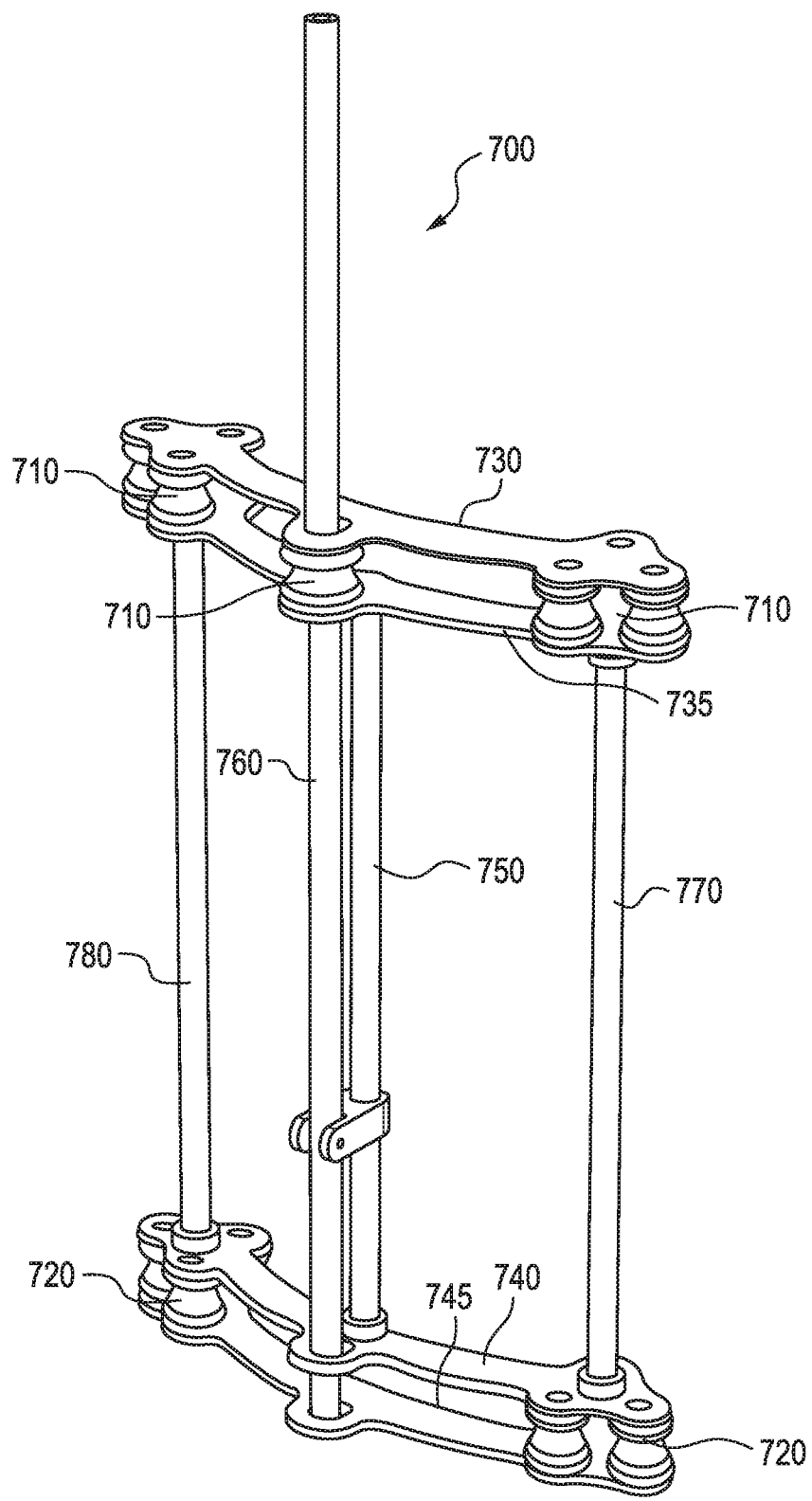
FIG. 12 illustrates a cantilever support with multiple bearings.

The lateral movement of the cantilever support along the body frame may also be improved by the use of multiple bearings. Preferably, the cantilevered protraction device includes a plurality of bearings on the upper and lower rails of the body frame. FIG. 12 illustrates a cantilever support with multiple bearings. The cantilever support 700 includes a plurality of upper bearings 710 and a plurality of lower bearings 720, which engage with the upper and lower rails of a body frame (not shown), respectively. The upper bearings are coupled together by a first upper bearing plate 730 and a second upper bearing plate 735. The lower bearings are coupled together by a first lower bearing plate 740 and a second lower bearing plate 745. The upper bearing plates and the lower bearing plates are coupled to a first shaft 750, a second shaft 760, a third shaft 770 and a fourth shaft 780. The use of multiple bearings helps to distribute the load across a wider distance, which reduces the moment load on each individual bearing. The use of multiple bearings is especially helpful for patients receiving larger protractionary forces for therapy, such as mature patients.

Figure 13:
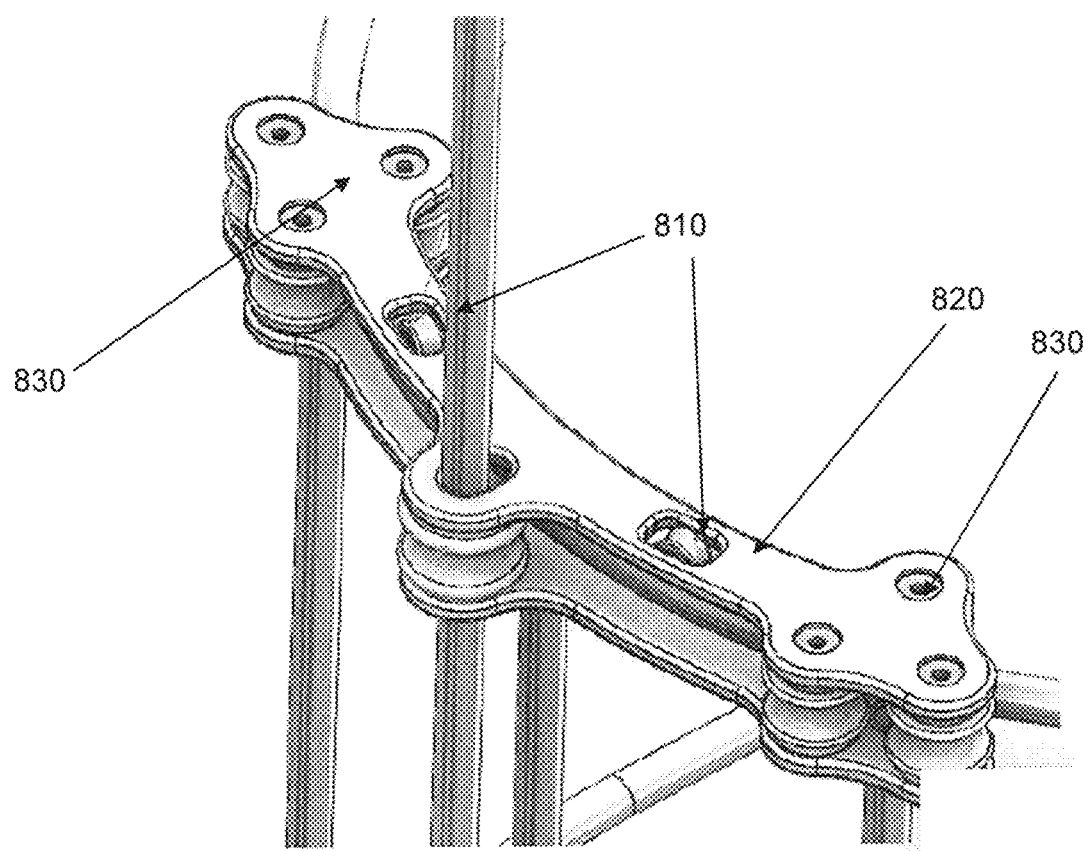
FIG. 13 illustrates a cantilever support with vertical rollers.

The cantilever support may optionally include additional rolling members to facilitate the lateral movement of the cantilever support along the body frame. FIG. 13 illustrates a cantilever support with vertical rollers. Vertical rollers 810 may be coupled to a bearing plate 820 between roller bearings 830. The vertical rollers may be coupled to any of the bearing plates. Additional rolling members may be used to smooth the lateral motion of the cantilever support when exposed to vertical loads.

In addition to securing the multiple bearings, the upper and lower bearing plates shown in FIGS. 12 and 13 improve the stability of the cantilever protraction device. Using a single plate to couple multiple bearings ensures that the roller bearings stay properly aligned with each other and with the rails of the body frame. In addition, the upper and lower bearing plates ensure that the first shaft and the second shaft maintain a proper vertical alignment. Maintaining vertical alignment of the first shaft and the second shaft is particularly important since these components may impair the lateral movement of the roller bearings if they become misaligned.

The use of multiple bearings allows for various geometries of the bearings and upper and lower plates. The separation angle of the bearings relative to the first shaft and the second shaft may be varied to provide a desired stability and movement profile. A wider separation angle spreads the moment loads and improves bearing performance. However, a wider angle will reduce the range of motion of the user's neck. A pair of roller bearings may have a separation angle of 15-90°. Preferably, a pair of roller bearings has a separation angle of 30-60°. More preferably, a pair of roller bearings has a separation angle of 45° or 60°. FIG. 14A illustrates a cantilever support with multiple bearings having a separation angle of 60°. FIG. 14B illustrates a cantilever support with multiple bearings having a separation angle of 45°. FIG. 14C illustrates a cantilever support with multiple bearings having a separation angle of 30°.

Figure 24:
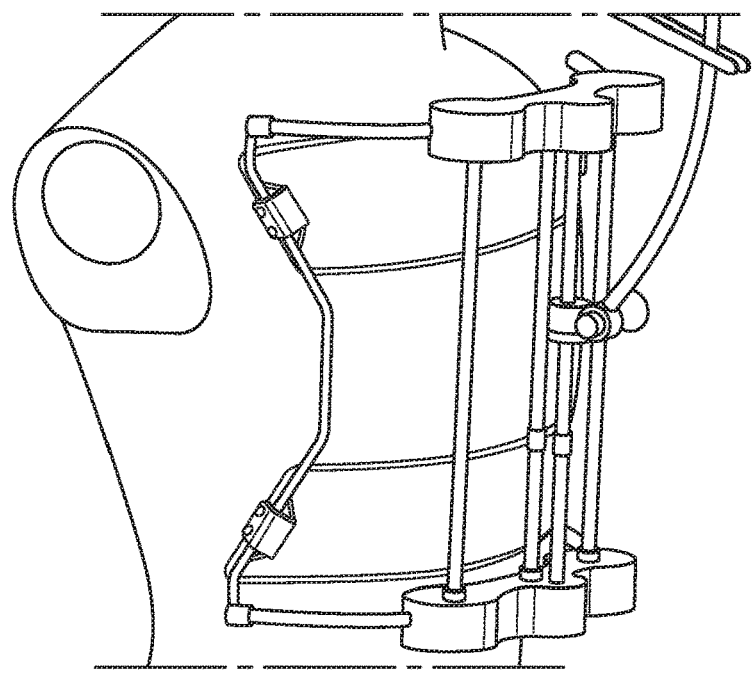
FIG. 24 illustrates a partial view of a cantilever protraction device with concealed bearings.

The bearings may optionally be concealed in a housing. FIG. 24 illustrates a partial view of a cantilever protraction device with concealed bearings. Concealing the bearings protects the bearings from material that could impact their functioning, such as dirt or food, and prevents objects from being caught in the bearings, such as clothing or a patient's hair.

Figure 17:
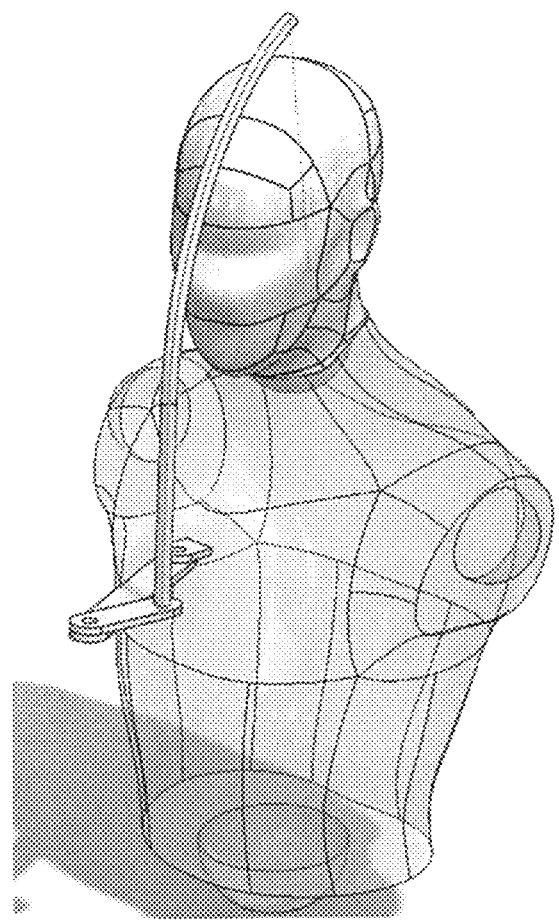
FIG. 17 illustrates a cantilever support coupled to a rotational hinge.

In an alternative configuration, a rotational hinge may be used to provide lateral movement of the cantilever support about the body frame. FIG. 17 illustrates a cantilever support coupled to a rotational hinge, which may be coupled to a body harness (not shown).

The stability of the cantilever protraction device may be increased by including support bars between the first shaft and the second shaft of the cantilever support. FIG. 15 illustrates a cantilever support with support bars. A plurality of support bars 910 are coupled to a first shaft 920 and a second shaft 930. The support bars are located between a first bearing 940 and a second bearing 950. The support bars offer additional support beyond that provided by the clamps that couple the first shaft to the second shaft (see FIG. 4, element 306). Alternatively, the clamps may be replaced by support bars. The use of multiple support bars further improves the stability of the cantilever protraction device by reducing the moments applied to the bearings.

Figure 18:
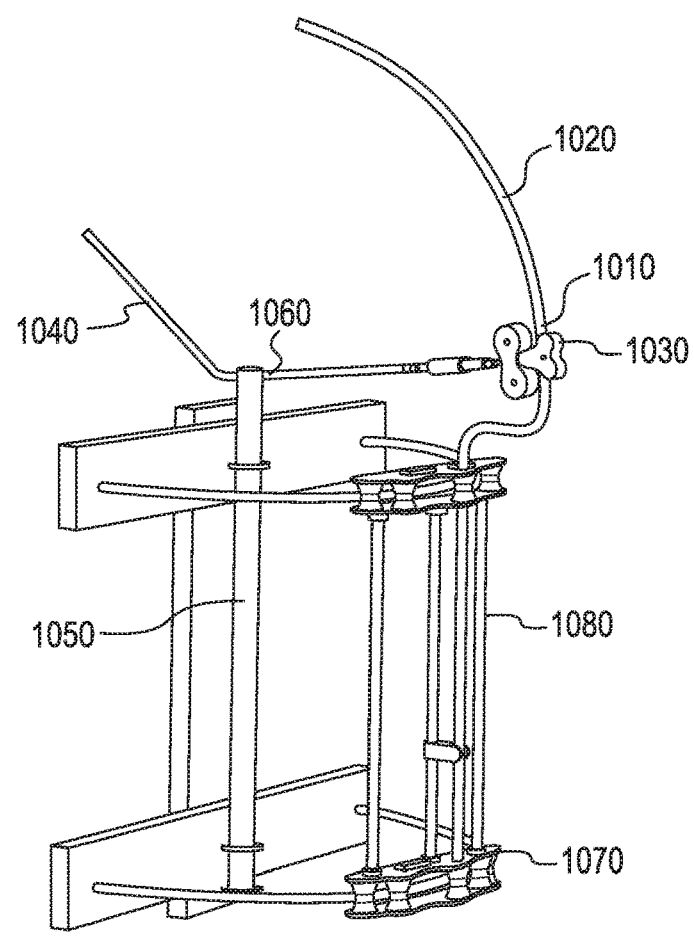
FIG. 18 illustrates a cantilever protraction device coupled to a moveable anchorage.

The comfort of the cantilever protraction device may be improved by including components that enhance the ability of a user to tilt, nod and rotate his or her head while wearing the device. FIG. 18 illustrates a cantilever protraction device coupled to a moveable anchorage. The cantilever protraction device includes a force applicator 1010 coupled to a headpiece rail 1020 by a roller bearing 1030. The headpiece rail is coupled to a cantilever support 1070 including a shaft 1080. The headpiece rail and the shaft of the cantilever support may be monolithic. The force applicator is coupled to a therapeutic appliance (not shown) by a protraction wire 1040. The protraction wire is coupled to a rotating post 1050 by a hinge 1060, which represent the head and neck of a patient. The patient may tilt, nod and rotate his or her head while wearing the device and still receive a constant protractionary force during movement. The rotating post and hinge demonstrate that it is feasible to have the patient move the force applicator and the cantilever support by moving the protraction wire with his or her head.

Figure 20A:
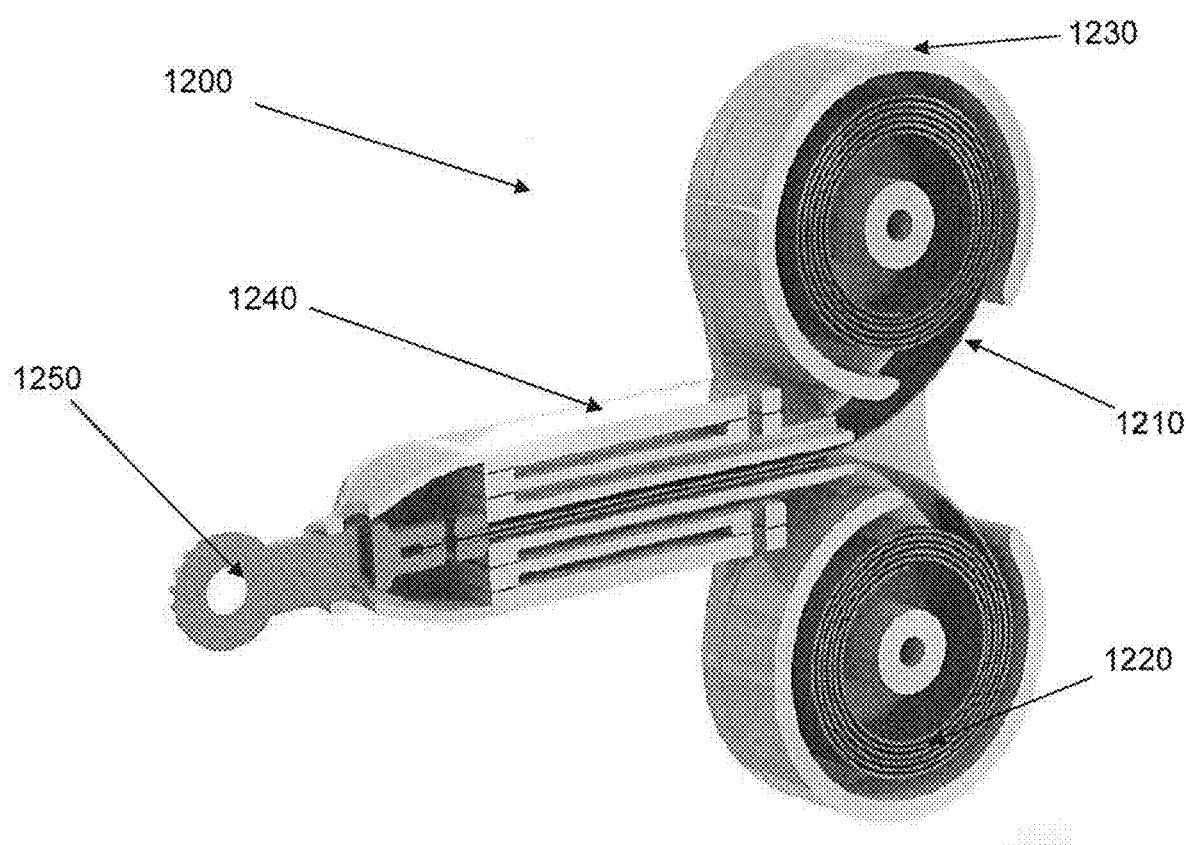
FIG. 20A illustrates a sectioned view of a force applicator including a constant-force spring.
Figure 20B:
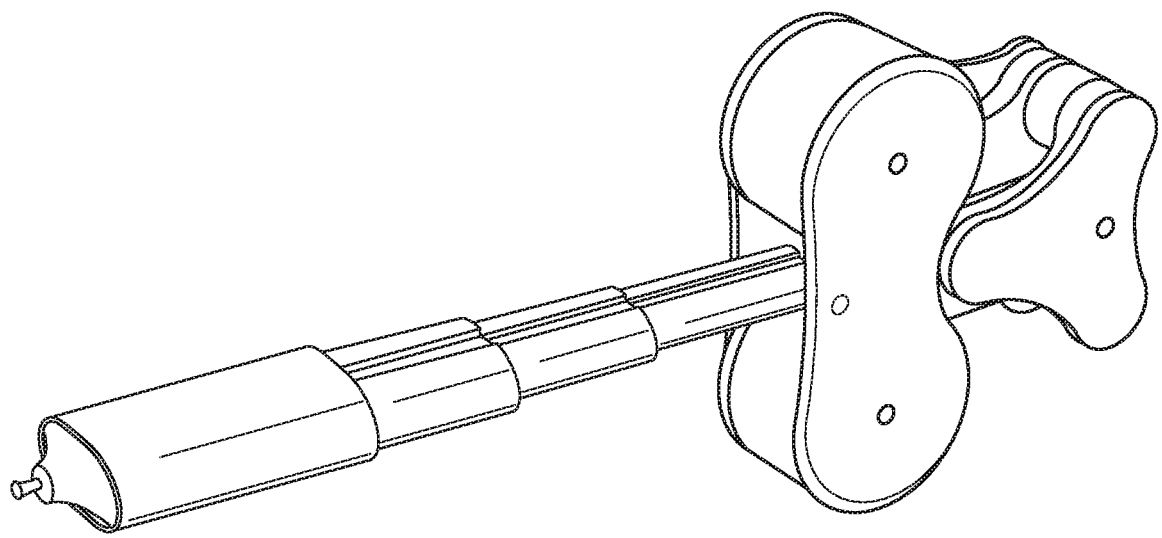
FIG. 20B illustrates a force applicator including a constant-force spring in an extended position.

The force applicator preferably provides a constant force throughout the range of motion when the user tilts, nods or rotates his or her head while wearing the device. A preferred force applicator is a constant-force spring. FIG. 20A illustrates a sectioned view of a force applicator including a constant-force spring. The force applicator 1200 includes a first constant-force spring 1210 and a second constant-force spring 1220 within a housing 1230. The housing includes a telescoping sleeve 1240 that protects the spring when it is extended. The force applicator includes an attachment point 1250 for coupling the force applicator to a therapeutic appliance (not shown). FIG. 20B illustrates a force applicator including a constant-force spring in an extended position. The force applicator preferably includes hard stops (not shown) to prevent overextension of the constant-force spring and exposure of the edges of the spring.

The force applicator may be removably coupled to a mount that is in turn coupled to a protraction device. FIG. 20C illustrates a force applicator 1200 and a mount 1260 for coupling the force applicator to a protraction device (not shown). The force applicator may be removably coupled to the mount by a mechanical fastener, such as a screw or spring mechanism, or by non-mechanical means, such as magnets or friction (press fit or snap-fit). The mount includes a roller bearing 1270 that may be coupled to a protraction device (see FIG. 18 and FIG. 19B).

Force applicators may provide different amounts of force by varying the width, thickness and/or diameter of the constant-force springs within the force applicator. The force applicator may be configured to provide any suitable therapeutic force. Preferably, the force applicator provides 0.1-10 kg of force.

Figure 21:
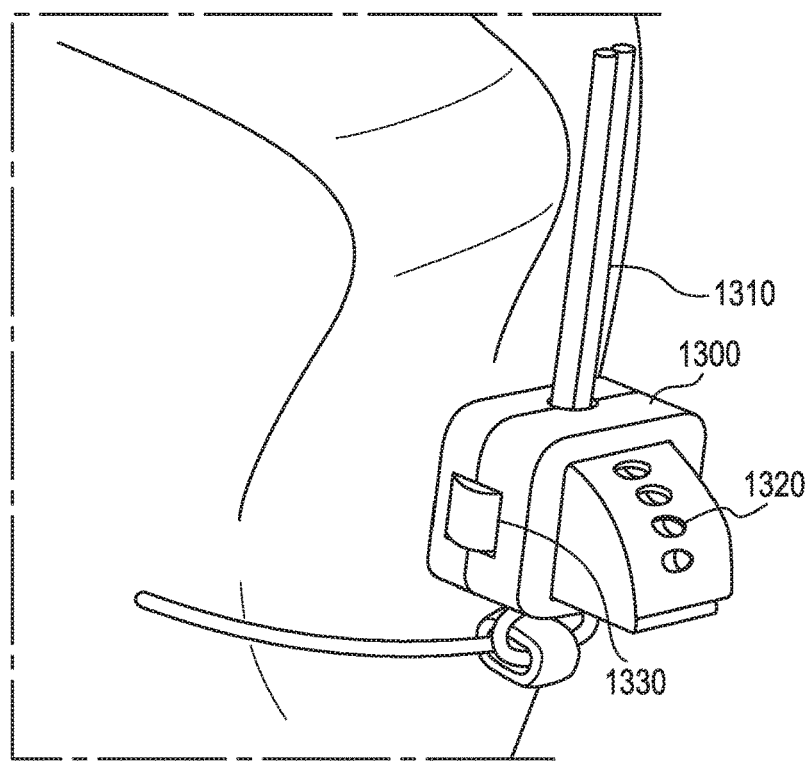
FIG. 21 illustrates an adjustable anchorage device coupled to a protraction wire.

The force applicator may be coupled to a therapeutic appliance through an adjustable anchorage device. FIG. 21 illustrates an adjustable anchorage device 1300 coupled to a protraction wire 1310. The adjustable anchorage device includes a plurality of holes 1320 for receiving a force applicator (see FIG. 19B). The holes may provide a range of angles for the force applicator, such as 0°-45°, including 5°, 10°, 15°, 20°, 25°, 30°, 35° and 40°. The adjustable anchorage device may be removably coupled to the protraction wire by actuating a release mechanism 1330. The adjustable anchorage device may be removably coupled to the protraction wire by a mechanical fastener, such as a screw or spring mechanism, or by non-mechanical means, such as magnets or friction (press fit or snap-fit).

The comfort of the cantilever protraction device may also be improved by customizing the body frame (see FIG. 2). One way to adjust the body frame is by making the strap pads on the body frame removable. For example, the strap pads may be removably coupled to the body frame using fasteners such as snaps, hook and loop fasteners or buckles. The use of removable strap pads allows the fit of the device to be customized to each specific user. For example, strap pads with differing levels of padding or differing levels of flexibility may be selected to provide a desired fit. The strap pads are preferably machine washable. Another way to adjust the body frame is by varying the geometry of the body frame rails. For example, the body frame rails may be straight, angled, curved, or some combination of these geometries. The customization of the body frame will promote a comfortable fit and promote user compliance.

Reducing the weight of the cantilever protraction device significantly improves the comfort for the user. The cantilever protraction device preferably includes materials that have high strength, high rigidity and low weight. Examples of suitable materials include aluminum, titanium, and carbon fiber.

The weight of the cantilever protraction device may be reduced by the use of hollow rather than solid components. For example, the rails of the body frame may be hollow tubes. Preferably, the hollow tubes are circular in cross section. The use of tubular rails in the body frame facilitates the movement of the bearings along the rails. The use of hollow components also reduces the cost of manufacturing the cantilever protraction device. Hollow tubes are readily available, easy to manufacture and inexpensive. Hollow aluminum tubes are a particularly preferred material for use in the body frame.

Figure 19A:
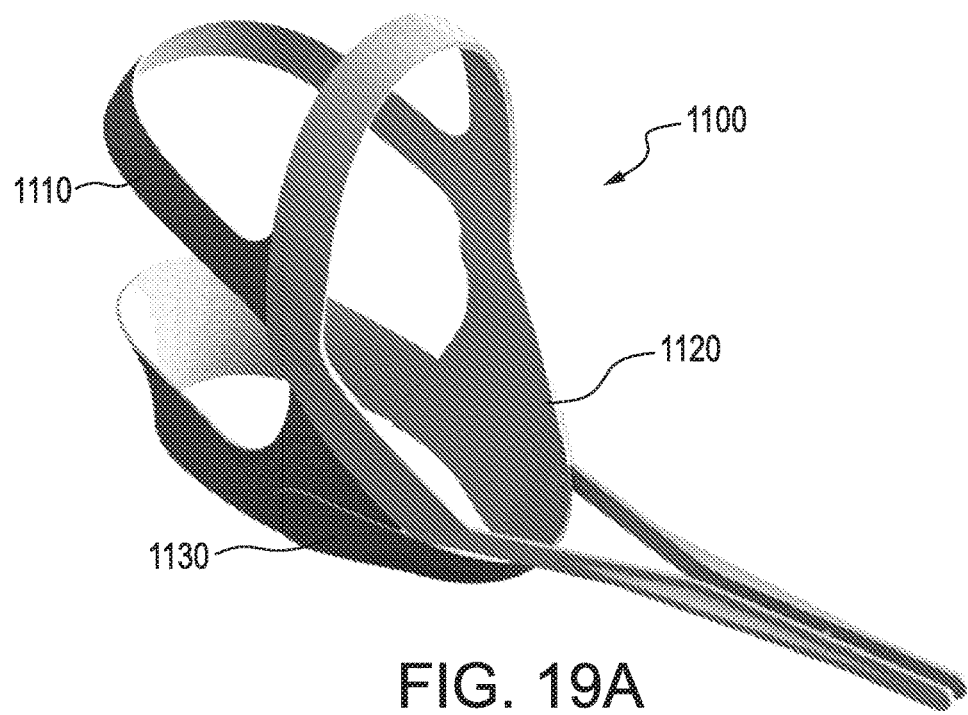
FIG. 19A illustrates a headpiece for a cantilever protraction device.

The comfort of the cantilever protraction device may be significantly improved by modifying the headpiece of the device. FIG. 19A illustrates a headpiece for a cantilever protraction device. The headpiece 1100 includes straps 1110 coupled to a harness 1120. The headpiece may optionally include a mandible strap 1130. The straps and the harness may optionally include pads on the side that contacts the user's head for comfort. The configuration of the mandible strap may be varied to provide a customized fit for the user. For example, the mandible strap may be configured to pass over or under the user's chin. In addition, the mandible strap may be configured to secure to both sides of a user's head. The harness may be formed from any rigid, durable material such as metals, plastics or ceramics. Preferably, the harness is made of plastic.

Figure 19B:
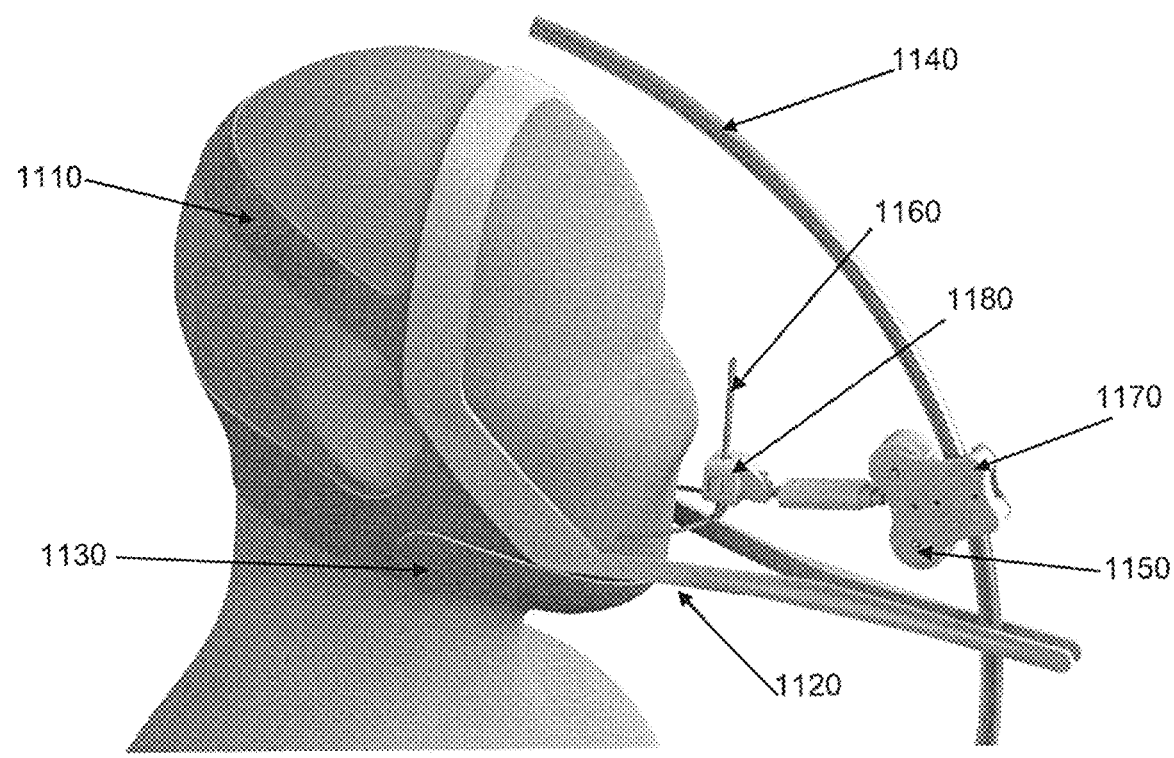
FIG. 19B illustrates a headpiece for a cantilever protraction device as worn by a user.
Figure 20C:
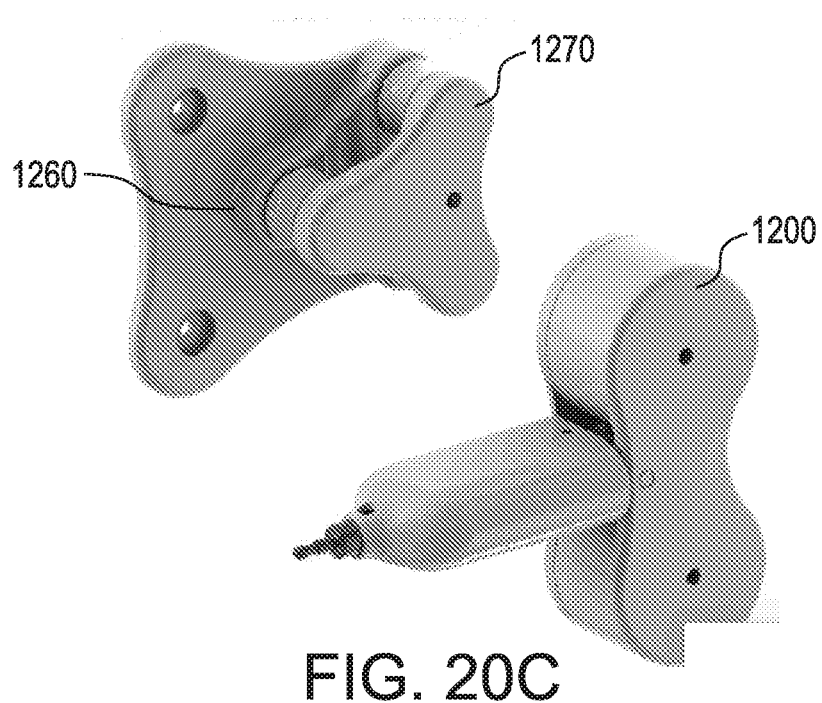
FIG. 20C illustrates a force applicator and a mount for coupling the force applicator to a protraction device.

FIG. 19B illustrates a headpiece for a cantilever protraction device as worn by a user. The straps 1110 are secured above and below the user's ears. The mandible strap 1130 passes under the user's chin. The harness 1120 is coupled to a headpiece rail 1140. A force applicator 1150 is coupled to a protraction wire 1160 and is coupled to the headpiece rail by a roller bearing 1170. The protraction wire is coupled to a therapeutic appliance (not shown) by an adjustable anchorage device 1180. The harness is preferably coupled to the headpiece rail close to the protraction wire to provide optimum support. Unlike conventional protraction devices, the harness does not obstruct the facial area of the user. Having an unobstructed facial area will improve comfort and facilitate use by users who wear eyeglasses or sunglasses.

Figure 25A:
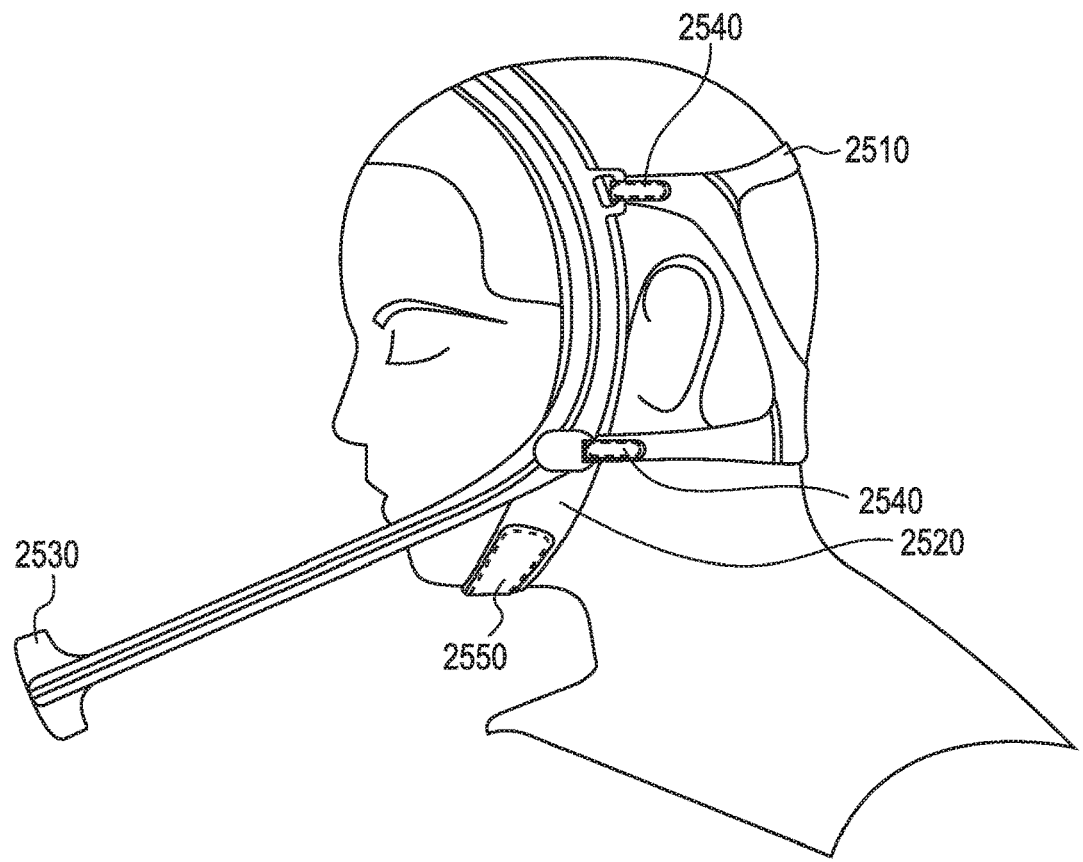
FIG. 25A illustrates a side view of an alternative design of a headpiece for a cantilever protraction device as worn by a user.
Figure 25B:
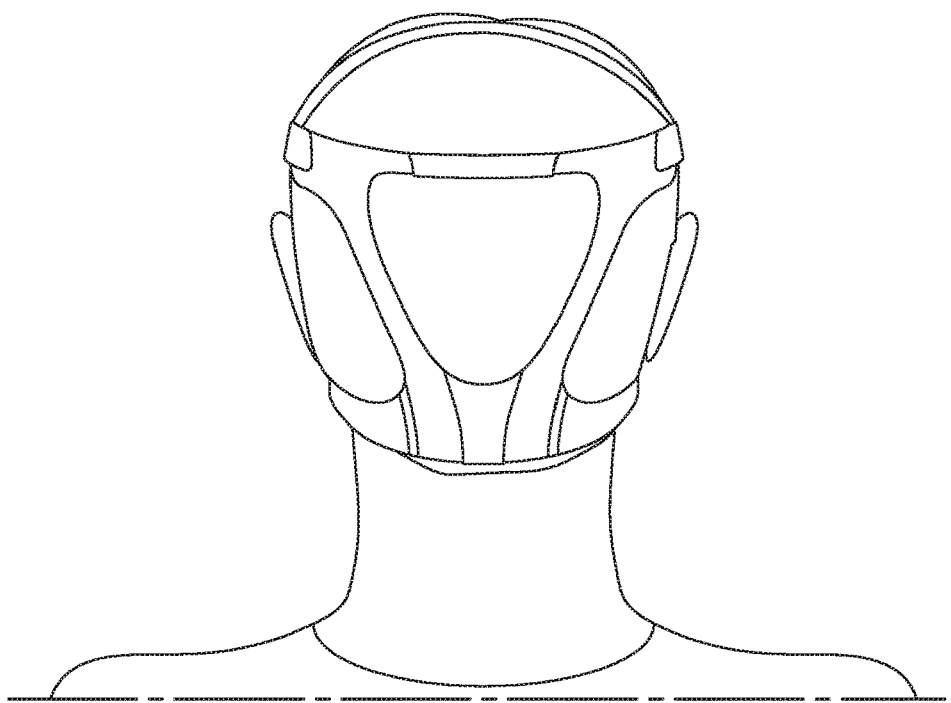
FIG. 25B illustrates a back view of an alternative design of a headpiece for a cantilever protraction device as worn by a user.

FIG. 25A illustrates a side view of an alternative design of a headpiece for a cantilever protraction device as worn by a user. FIG. 25B illustrates a back view of the headpiece. The headpiece includes a first strap 2510 that encircles the back and sides of the user's head and a second strap 2520 that passes under the user's mandible and is removably coupled to the user's head with a mandible fastener 2550. A harness 2530 is coupled to the second strap and is removably coupled to the first strap by a plurality of harness fasteners 2540 and to a protraction device (not shown). The mandible and harness fasteners are adjustable to provide a customized fit. The fasteners may be any suitable type of removable fastener, such as a hook and loop (VELCRO®) fastener, a magnetic fastener or a snap fastener. In addition to improving the comfort of the headpiece, the fasteners may also simplify the process of attaching and removing the headpiece from the user's head. For example, a user may customize the fit of the first strap and secure the harness to the first strap with hook and loop harness fasteners. The headpiece may then be attached to or removed from the user's head by fastening or unfastening a magnetic mandible fastener near the user's chin or cheek without the need to readjust the harness fasteners.

Figure 16:
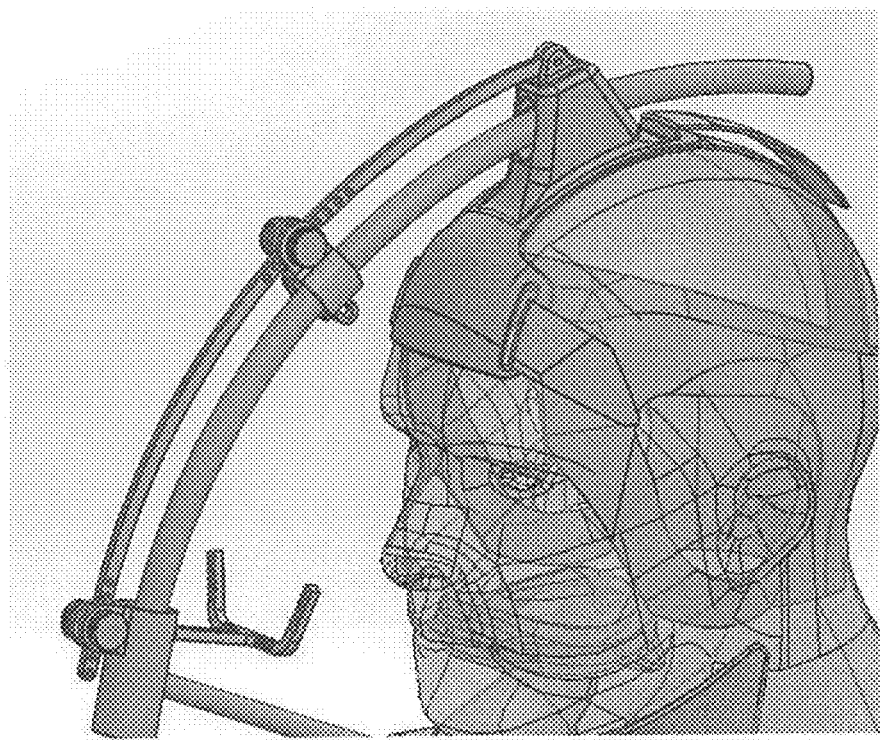
FIG. 16 illustrates a cantilever protraction device with a neck support.

The headpiece may optionally include a neck support. FIG. 16 illustrates a cantilever protraction device with a neck support. The neck support may be used to apply forces on the mandible or support the neck during therapy.

The updated headpiece designs shown in FIGS. 19A and 19B offers significant advantages over the earlier headpiece design shown in FIGS. 1-9. Components such as the linkage bar (FIG. 5, element 408) and the rail guide (FIG. 5, element 404) may be eliminated, which reduces cost and the weight of the device. The use of a rigid force applicator and roller bearings in the updated headpiece design also improves the functionality of the device. The earlier headpiece design required the user to use his or her head to direct the movement of the cantilever support along the body frame and the movement of the headpiece components along the headpiece rail. This head-based movement resulted in undesired forces on the user's head and neck areas. By contrast, in the updated headpiece design the rigid force applicator assists in the movement of the device components, particularly when nodding. This allows the updated headpiece to be used to maintain the user's head in the proper position and assist with lateral motion of the cantilever support along the body frame, reducing the undesired forces on the user's head and neck areas.

A key feature of the cantilever protraction device is that it is universally compatible with any orthodontic and craniomaxillofacial (CMF) devices. The cantilever protraction device may be coupled to a therapeutic appliance anchored to the teeth, bone, such as the upper jaw or lower jaw, or soft tissue of a patient. For example, the cantilever protraction device may be coupled to the maxillary protraction devices described in WO 2019/018249 and WO 2019/104255. Similarly, any type of force applicator may be coupled to the cantilever protraction. For example, the force applicator may include springs, constant-force springs, elastics and wires.

Another key feature of the cantilever protraction device is that it does not apply any forces or loads to the head of the user. As shown in the figures and as described above, a headpiece is coupled to a cantilever support, but the cantilever support does not impart any forces to the user's head through the headpiece. For example, FIG. 5 illustrates that the rail 406 passes through an opening in the rail guide 404, but the rail does not rest on the rail guide or transmit any forces onto the head of the user. In the embodiment shown in FIG. 5, the rail and the rail guide only are in contact when the user moves his or her head laterally, which results in lateral movement of the cantilever support about the body frame.

A means for movably coupling a cantilever support to a body frame may be, for example, a slider bearing, a roller bearing, a vertical roller or a rotational hinge. A means for coupling the head of a patient to a cantilever support may be, for example, a headpiece, a head strap, a harness or a harness including a head strap and/or a mandible strap. A means for applying a protractionary force to the craniofacial complex of a patient may be, for example, a spring, a constant-force spring, elastics or a wire.

Protraction Wire Customization

A preferred application of the cantilever protraction device is use with a skeletal anchorage system to apply an extra-oral force, such as a protraction force, to an intra-oral skeletal anchorage. As described in WO 2019/018249 and WO 2019/104255, it is possible to apply non-rotational forward and forward and upward forces directly to the maxilla of a patient. This is preferable to conventional devices that involve attaching elastics to an intra-oral anchorage, which results in an unnatural downward pull and/or rotational pull on the maxillary complex.

The extra-oral forces may be applied to the intra-oral skeletal anchorage using an orthodontic appliance that can be described as a modified orthodontic facebow, wire or protraction wire. The orthodontic appliance may be removably coupled to the skeletal anchorage by the patient or his or her caregiver. Due to the natural variation in each patient's oral and bone geometry, the positioning of the skeletal anchorage device and the configuration of the protraction wire must be customized for each patient.

A method of customizing a protraction wire includes determining a patient's oral and/or bone geometry; and adjusting the protraction wire. The protraction wire includes an intra-oral portion that is located inside the mouth of the patient and an extra-oral portion that is located outside of the mouth of the patient. The intra-oral portion of the protraction wire may be adjusted to match the patient's oral and/or bone geometry. For example, the protraction wire may be adjusted to minimize interference and/or friction with the lips, cheeks, teeth, gingiva, and the tongue to minimize disruption of biological functions. The extra-oral portion of the protraction wire may be adjusted to provide a specific therapeutic force application. For example, if the patient requires lateral force application to the skeletal anchorage point, the width of the protraction wire may be increased to impart a desired lateral force. Adjusting the protraction wire may involve adjusting the intra-oral portion of the protraction wire, the extra-oral portion of the protraction wire or both the intra-oral and the extra-oral portions of the protraction wire. Any adjustments to the protraction wire must maintain optimal coupling with a skeletal anchorage device.

The protraction wire may be composed of any substance that is sufficiently rigid to transmit therapeutic forces to the patient and that is sufficiently malleable to be adjusted to fit the patient's specific oral and/or bone geometry. For example, the protraction wire may be composed of spring temper wire or annealed wire. A preferred protraction wire material is 17-7 PH stainless steel.

A patient's oral and/or bone geometry may be determined using any suitable means for measuring and recording the details of the patient's oral and/or bone geometry. Examples of measuring and recording techniques include obtaining an impression, such as by dental casting or molding, and obtaining a digital measurement, such as by a digital scan or cone beam computed tomography (CBCT). A physical or digital model of the patient's oral and/or bone geometry may be created from the recorded measurements.

The protraction wire may be adjusted manually. A physical model of the patient's oral and/or bone geometry may be coupled to a dental rig. A protraction wire may then be adjusted by hand or using tools to match the model of the patient's oral and/or bone geometry to provide a specific therapeutic force application.

The protraction wire also may be adjusted digitally. A three-dimensional (3D) model of the patient's oral and/or bone geometry may be created from a digital measurement using a 3D software module. A digital model of a protraction wire may be adjusted to match the digital model of the patient's oral and/or bone geometry to provide a specific therapeutic force application. The digital model of the protraction wire may be submitted to a wire former to manufacture the customized protraction wire, or may be used to produce a customized protraction wire using a desktop 3D wire former. Machine learning may optionally be used to accelerate the digital adjustment process.

Adjusting the protraction wire may optionally involve the input of a medical professional experienced with orthodontic and craniomaxillofacial (CMF) therapy. For example, the medical professional may be a doctor, a dentist, an orthodontist or an assistant/technician working under the supervision of the medical professional. The medical professional may aid in determining the appropriate therapeutic force vectors to provide a desired therapeutic outcome.

The protraction wire may optionally be treated after customization. For example, a customized protraction wire may be heat treated to reach a desired hardness and yield strength. The protraction wire may be treated by the person who customizes the wire. Alternatively, the protraction wire may be treated at a separate facility in a different physical location from the customization.

Figure 23:
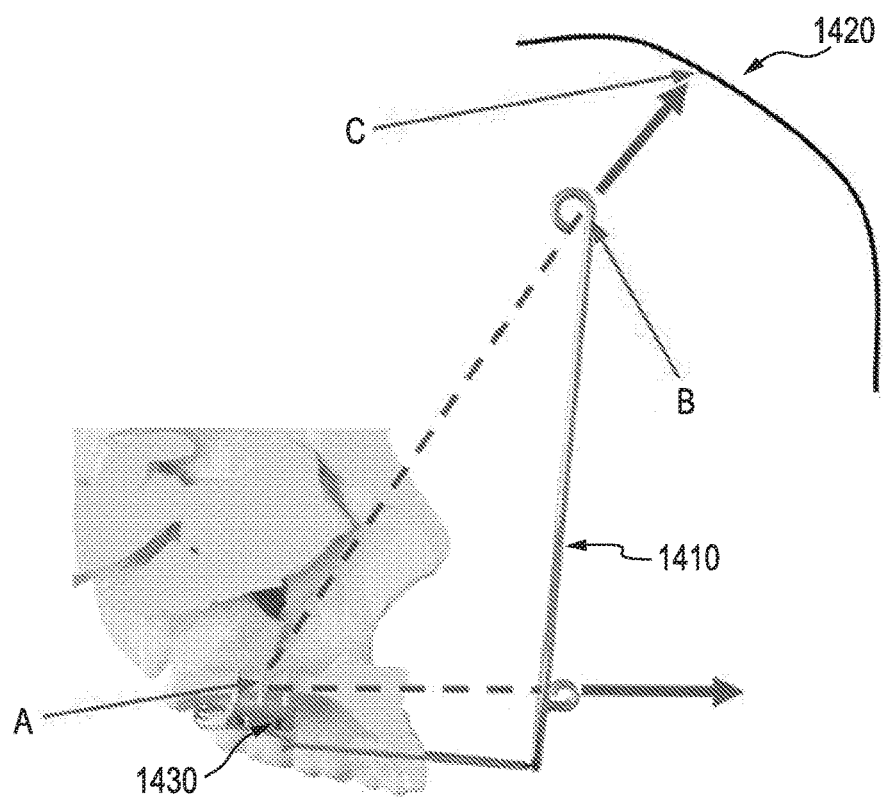
FIG. 23 illustrates a protraction wire coupled to a protraction device and to a skeletal anchorage.

FIG. 23 illustrates a protraction wire 1410 coupled to a protraction device 1420 and to a skeletal anchorage 1430. A non-rotational forward and/or forward/upward force vector may be applied to the patient's maxilla along a desired force vector of 0°-75° by aligning the skeletal anchorage (Point A), the protraction wire (Point B) and the protraction device (Point C). The appropriate location of the skeletal anchorage, the protraction wire and the protraction device is unique to each patient and is determined by the patient's oral and/or bone geometry and therapeutic force needed. The protraction wire may be customized as discussed above. The protraction wire and the protraction device may optionally be configured to provide adjustable force vectors. For example, the protraction wire may be coupled to the protraction device by an adjustable force applicator and an adjustable anchorage device (see FIG. 19B). Similarly, the protraction wire may include multiple attachment points or notches to provide variable force vectors.

The several components of the present invention described above can be constructed using any suitable method known in the art. The method of making may vary depending on the materials used. For example, components substantially comprising a metal may be milled from a larger block of metal or may be cast from molten metal. Likewise, components substantially comprising a plastic or polymer may be milled from a larger block, cast, or injection molded. In some embodiments, the devices may be made using 3D printing or other additive manufacturing techniques commonly used in the art.

EXAMPLES

The invention is further described in detail by reference to the following experimental examples. These examples are provided for purposes of illustration only, and are not intended to be limiting unless otherwise specified. Thus, the invention should in no way be construed as being limited to the following examples, but rather, should be construed to encompass any and all variations which become evident as a result of the teaching provided herein.

Without further description, it is believed that one of ordinary skill in the art can, using the preceding description and the following illustrative examples, make and utilize the compounds of the present invention and practice the claimed methods. The following working examples therefore, specifically point out exemplary embodiments of the present invention, and are not to be construed as limiting in any way the remainder of the disclosure.

Example 1: Low Friction Bearing Prototyping

A low friction bearing was attached to a leveled aluminum tube and a known weight was hung from the bearing to apply a normal force. A container was attached to the same bearing and the wire was run perpendicularly to and hung from a pulley wheel. Weights were added to the container to determine the amount of lateral force needed to move the bearing and overcome the normal force applied by the known weight.

Figure 10:
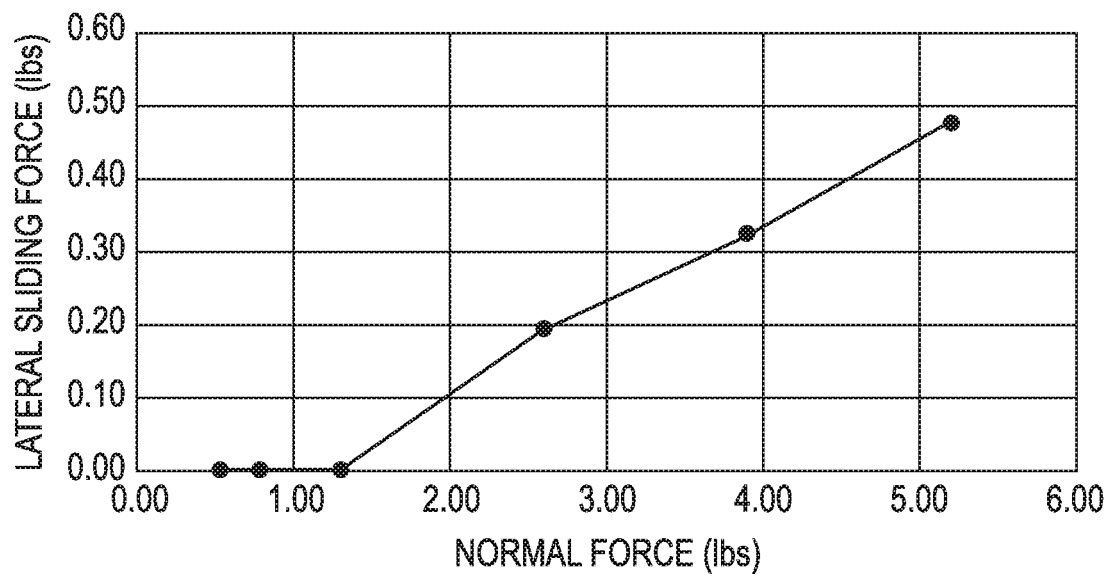
FIG. 10 depicts the results of experiments investigating the effect of normal force on the lateral force needed to move a low friction bearing along an aluminum rail.

Results are shown in FIG. 10. The lateral force required to initiate sliding in the bearing is more than an order of magnitude less than the applied therapeutic loads. For example, the nominal case of 2.2 lbs forward force plus 2.2 lbs upward force has a resultant force of $(2.2^2+2.2^2)^{0.5}=3.1$ lbs. This would require 0.26 lbs of a head turning force to initiate sliding. An extreme case of 4.4 lbs forward force plus 4.4 lbs upward force has a resultant force of $(4.4^2=4.4^2)^{0.5}=6.2$ lbs. This would require 0.52 lbs head turning force. The initiation force is the peak force needed to start motion from a dead stop. Once motion is started, the friction (and subsequent forces) can drop by as much as 50%.

Example 2: Finite Element Analysis (FEA) of Headpiece Harness

Figure 22A:
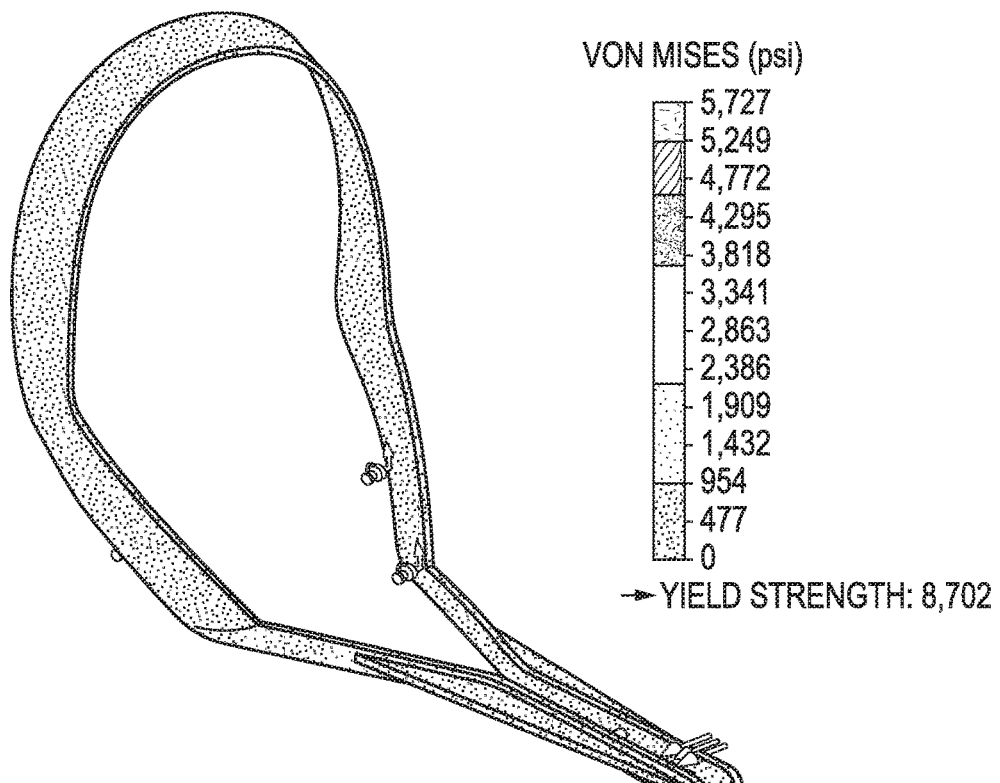
FIG. 22A illustrates the finite element analysis of the von Mises stresses of a harness for a cantilever protraction device as measured in pounds per square inch (psi).
Figure 22B:
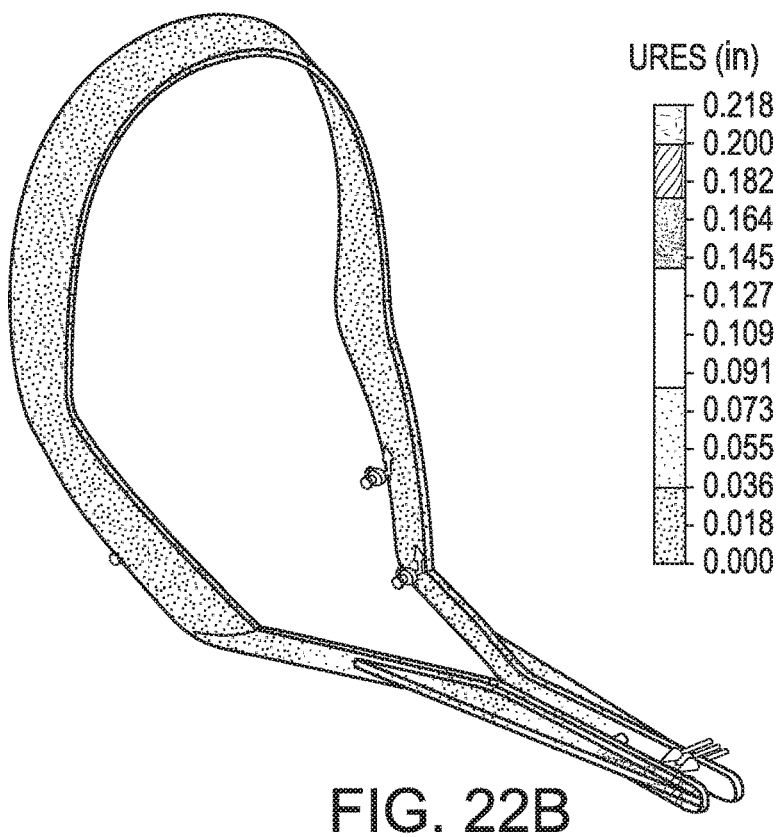
FIG. 22B illustrates the finite element analysis of the URES displacement of a harness for a cantilever protraction device as measured in inches.

A finite element analysis (FEA) was performed on the headpiece harness shown in FIGS. 19A and 19B. The FEA modeled the stresses and displacements on the harness when subjected to up to 2 lbs of pushing force. FIG. 22A illustrates the finite element analysis of the von Mises stresses of the harness as measured in pounds per square inch (psi). FIG. 22B illustrates the finite element analysis of the URES displacement of the harness as measured in inches. The harness exhibited acceptable stresses and displacement with up to 2 lbs of pushing force.

Example 3: Use of Cantilever Protraction Device with Acrylic Appliance

The BIOBLOC™ acrylic appliance is a commercially available therapeutic appliance used to generate craniofacial skeletal corrections to treat craniofacial dystrophy. The BIOBLOC™ appliance is suitable for adolescent patients who have open sutural system/synchondroses (growth centers) in their maxillofacial complex, which prevents the need for skeletal anchorage. The conventional use of the BIOBLOC™ appliance involves coupling the appliance to a protraction wire that extends towards the patient's ears. This design is uncomfortable for patients, particularly when the appliance is worn overnight since it impacts the ability of patients to sleep comfortably on their sides. In addition, the use of a protraction wire that extends towards the ears results in a force vector that extends in a different direction than the other therapeutic forces provided by the protraction device.

Figure 26A:
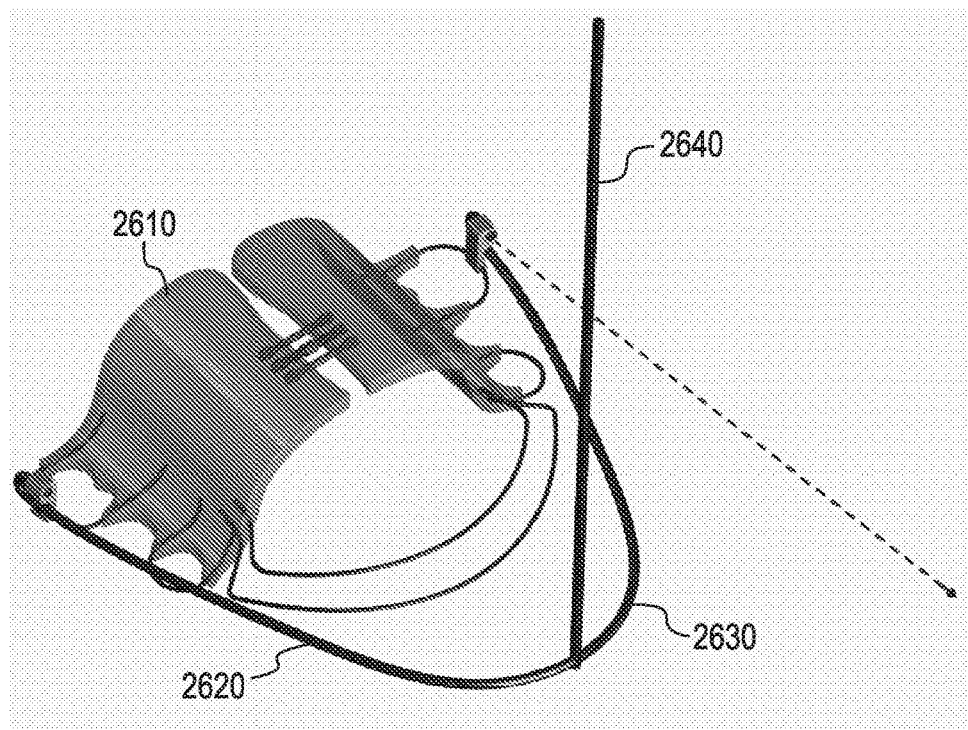
FIG. 26A illustrates a perspective view of a therapeutic appliance coupled to a trans-oral member.

FIG. 26A illustrates a perspective view of a therapeutic appliance 2610 coupled to a trans-oral member 2620. The trans-oral member includes a curved member 2630 and an extra-oral vertical member 2640. The therapeutic appliance is adapted to be coupled to at least one member selected from the group consisting of the teeth, bone, and soft tissue of the patient. Each end of the curved member is coupled to opposing ends of the therapeutic appliance. The extra-oral vertical member extends vertically from the plane of the curved member, and may optionally extend perpendicularly or substantially perpendicularly from the curved member. The trans-oral member may be coupled to a protraction device (not shown), such as the cantilever protraction device described herein.

Figure 26B:
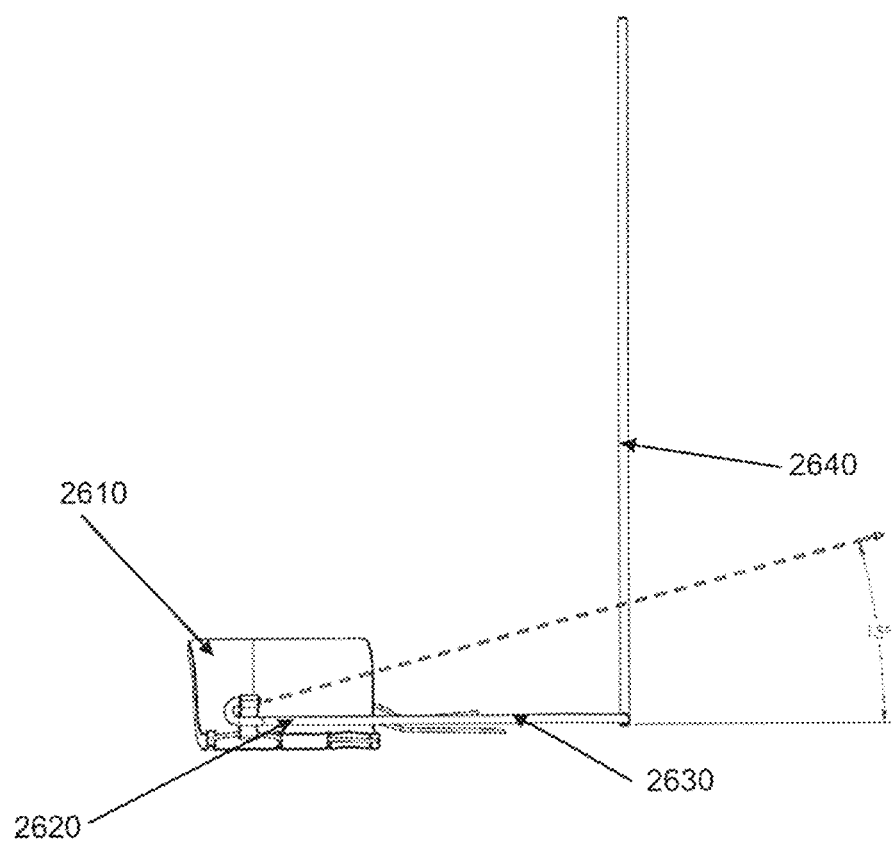
FIG. 26B illustrates a side view of a therapeutic appliance coupled to a trans-oral member.

The dashed line in FIG. 26A represents the direction of the force vector. FIG. 26B illustrates a side view of the therapeutic appliance coupled to the trans-oral member. The dashed line in FIG. 26B indicates that the force vector extends at an angle of 15° relative to the trans-oral member. Importantly, the force vector extends in the same direction as the trans-oral member and any protractionary forces imparted by an extraoral force applicator (not shown). Preferably, the protractionary forces are only applied through the extra-oral vertical member.

It should be understood that the BIOBLOC™ appliance is exemplary of any tooth-anchored appliance. Applying protraction forces to any tooth-anchored appliance provides the same result: the protraction forces are transmitted to the tooth roots and from there to the palatal vault. The trans-oral member may be attached to any type of tooth-anchored appliance, including directly to molar attachments without any palatal components.

The disclosures of each and every patent, patent application, and publication cited herein are hereby incorporated herein by reference in their entirety. While this invention has been disclosed with reference to specific embodiments, it is apparent that other embodiments and variations of this invention may be devised by others skilled in the art without departing from the true spirit and scope of the invention. The appended claims are intended to be construed to include all such embodiments and equivalent variations.

REFERENCES

1. U.S. Pat. No. 8,640,710.
2. U.S. Pat. No. 10,166,089.
3. U.S. Patent Publication No. 2018/0028282.
4. Moon, W., "Class III treatment by combining facemask (FM) and maxillary skeletal expander (MSE)", Seminars in Orthodontics, Vol 24, No. 1, pp. 95-107 (2018).
5. International Patent Publication No. WO 2019/018249.
6. International Patent Publication No. WO 2019/104255.

What is claimed is:

1. A protraction device, comprising:
    a body frame, adapted to be anchored to the body of a patient,
    a cantilever support, including
        a first shaft, coupled to the body frame, and
        a second shaft, coupled to the first shaft, and
    a headpiece, including
        a head strap, adapted to couple to the head of the patient, and
        a headpiece rail, coupled to the second shaft and coupled to the head strap,
    wherein the headpiece rail is adapted to extend in front of the face of the patient,
    the body frame comprises
        a top rail, and
        a bottom rail, and
    the cantilever support further comprises
        a top bearing, coupled to the top rail, and
        a bottom bearing, coupled to the bottom rail, and
    the first shaft is coupled to the top bearing and the bottom bearing.

2. The protraction device of claim 1, wherein the top bearing and the bottom bearing comprise roller bearings.

3. The protraction device of claim 1, wherein the headpiece comprises
    a harness, and
    the head strap, coupled to the harness, and
    the headpiece is coupled to the headpiece rail by the harness.

4. The protraction device of claim 3, wherein the head strap further comprises a mandible strap.

5. The protraction device of claim 3, wherein the harness does not obstruct the facial area of a patient.

6. The protraction device of claim 1, wherein the cantilever support comprises at least two top bearings and at least two bottom bearings,
    the at least two top bearings are coupled by a first top bearing plate and a second top bearing plate, and the at least two bottom bearings are coupled by a first bottom bearing plate and a second bottom bearing plate.

7. The protraction device of claim 6, wherein the first top bearing plate, the second top bearing plate, the first bottom bearing plate and the second bottom bearing plate are each monolithic.

8. The protraction device of claim 6, further comprising a low-friction substance between the roller bearings and the bearing plates.

9. The protraction device of claim 6, further comprising a vertical roller coupled to at least one of the upper bearing top plate, the upper bearing bottom plate, the lower bearing top plate and the lower bearing bottom plate.

10. The protraction device of claim 1, wherein the body frame further comprises a first side rail, coupled to one end of the top rail and the bottom rail,
   a second side rail, coupled to the opposite end of the top rail and the bottom rail, and
   a plurality of straps, coupled to the body frame.

11. The protraction device of claim 1, further comprising a force applicator mount, coupled to the headpiece rail by a bearing.

12. The protraction device of claim 11, further comprising a force applicator, removably coupled to the force applicator mount.

13. The protraction device of claim 12, further comprising a therapeutic appliance, coupled to the force applicator.

14. The protraction device of claim 13, wherein the therapeutic appliance is coupled to the force applicator by an adjustable anchorage device.

15. The protraction device of claim 1, wherein the top rail and the bottom rail each comprise hollow tubes.

16. The protraction device of claim 1, wherein
   the headpiece further includes a rail guide, coupled to the head strap, and having a lumen sized to fit the headpiece rail, and
   the headpiece rail passes through the lumen, to couple the headpiece rail to the head strap.

17. The protraction device of claim 16, wherein
   the headpiece further includes a first low friction bearing, and
   the first low friction bearing is coupled to the headpiece rail, and coupled to an attachment adapted for connecting to at least one of a string, wire, and elastic band.

18. The protraction device of claim 17, wherein the attachment is a hook attachment or a linear gear bar attachment.

19. The protraction device of claim 17, wherein
   the headpiece further includes a linkage bar, coupled to the rail guide, and
   the first low friction bearing includes a first lock, adapted to lock to the rail guide.

20. The protraction device of claim 17, wherein
   the headpiece further includes a second low friction bearing,
   the second low friction bearing is coupled to the headpiece rail, and coupled to an attachment adapted for connecting to at least one of a string, wire, and elastic band.

\* \* \* \* \*